US010980409B2

(12) United States Patent
Kikuchi

(10) Patent No.: US 10,980,409 B2
(45) Date of Patent: Apr. 20, 2021

(54) ENDOSCOPE DEVICE, IMAGE PROCESSING METHOD, AND COMPUTER READABLE RECORDING MEDIUM

(71) Applicant: OLYMPUS CORPORATION, Hachioji (JP)

(72) Inventor: Sunao Kikuchi, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 16/827,777

(22) Filed: Mar. 24, 2020

(65) Prior Publication Data

US 2020/0221942 A1 Jul. 16, 2020

Related U.S. Application Data

(63) Continuation of application No. PCT/JP2017/036189, filed on Oct. 4, 2017.

(51) Int. Cl.
*A61B 1/06* (2006.01)
*H04N 9/04* (2006.01)
(Continued)

(52) U.S. Cl.
CPC ........ *A61B 1/0638* (2013.01); *A61B 1/00006* (2013.01); *A61B 1/00009* (2013.01);
(Continued)

(58) Field of Classification Search
CPC .............. A61B 1/0638; A61B 1/00006; A61B 1/00009; A61B 1/051; A61B 1/0646;
(Continued)

(56) References Cited

U.S. PATENT DOCUMENTS

| 4,672,433 A * | 6/1987 | Yamamoto ............... | H04N 1/58 358/525 |
| 9,237,321 B2 * | 1/2016 | Kikuchi .................. | H04N 9/07 |

(Continued)

FOREIGN PATENT DOCUMENTS

| JP | S60139383 U | 9/1985 | |
| JP | 2009-284959 | * 12/2009 | ............... A61B 1/04 |

(Continued)

OTHER PUBLICATIONS

International Search Report (ISR) (and English translation thereof) dated Dec. 12, 2017 issued in International Application No. PCT/JP2017/036189.

(Continued)

*Primary Examiner* — James M Pontius
(74) *Attorney, Agent, or Firm* — Holtz, Holtz & Volek PC

(57) ABSTRACT

An endoscope device includes: a light source configured to perform any one of simultaneous lighting and sequential lighting; an image sensor including a plurality of pixels; a plurality of filters including at least one type of primary filter and a complementary filter; and a processor including hardware, the processor being configured to cause the light source to switch between the simultaneous lighting and the sequential lighting, when the simultaneous lighting is performed, perform interpolation processing to generate an output image by using an imaging signal generated from a pixel corresponding to the complementary filter, and when the sequential lighting is performed, perform interpolation processing to generate an output image by using an imaging signal generated from a pixel corresponding to the complementary filter as an imaging signal generated from a pixel corresponding to the at least one type of primary filter.

11 Claims, 17 Drawing Sheets

(51) Int. Cl.
*A61B 1/00* (2006.01)
*A61B 1/05* (2006.01)
*H04N 5/235* (2006.01)
*A61B 5/02* (2006.01)
*A61B 5/00* (2006.01)
*H04N 5/225* (2006.01)

(52) U.S. Cl.
CPC ............ *A61B 1/051* (2013.01); *A61B 1/0646* (2013.01); *H04N 5/2354* (2013.01); *H04N 9/0455* (2018.08); *A61B 5/02042* (2013.01); *A61B 5/4887* (2013.01); *H04N 2005/2255* (2013.01)

(58) Field of Classification Search
CPC . A61B 5/02042; A61B 5/4887; A61B 5/1128; A61B 5/0084; A61B 2576/00; A61B 2505/05; A61B 5/7207; A61B 1/05; A61B 1/07; A61B 1/045; H04N 9/0455; H04N 5/2354; H04N 2005/2255; H04N 9/04561; H04N 9/04515
See application file for complete search history.

(56) References Cited

U.S. PATENT DOCUMENTS

| | | | |
|---|---|---|---|
| 9,282,305 B2* | 3/2016 | Kikuchi | H04N 5/332 |
| 9,741,113 B2* | 8/2017 | Kikuchi | A61B 5/0077 |
| 9,843,782 B2* | 12/2017 | Kikuchi | G06T 3/4015 |
| 10,299,665 B2* | 5/2019 | Yoshizaki | H04N 9/04553 |
| 10,404,953 B2 | 9/2019 | Kikuchi | |
| 10,448,816 B2 | 10/2019 | Moriya | |
| 2006/0241496 A1* | 10/2006 | Fengler | A61B 1/0638 600/476 |
| 2008/0316343 A1* | 12/2008 | Min | G06F 12/1458 348/294 |
| 2011/0176730 A1* | 7/2011 | Sasaki | G06T 3/4015 382/167 |
| 2012/0206582 A1* | 8/2012 | DiCarlo | A61B 1/0005 348/71 |
| 2015/0042775 A1* | 2/2015 | Zhao | H04N 9/04557 348/71 |
| 2015/0092032 A1* | 4/2015 | Kuramoto | H05B 45/37 348/68 |
| 2015/0094537 A1* | 4/2015 | Kuramoto | A61B 1/00057 600/160 |
| 2016/0270643 A1 | 9/2016 | Sasaki | |
| 2017/0251915 A1* | 9/2017 | Takahashi | A61B 1/00059 |
| 2017/0258304 A1 | 9/2017 | Ioka et al. | |
| 2017/0265731 A1* | 9/2017 | Yoshizaki | H04N 5/33 |
| 2017/0276847 A1 | 9/2017 | Yoshizaki et al. | |
| 2017/0280122 A1* | 9/2017 | Sato | H04N 5/2354 |
| 2017/0325658 A1 | 11/2017 | Ioka et al. | |
| 2018/0010966 A1* | 1/2018 | Ichikawa | G01J 3/027 |
| 2018/0234650 A1* | 8/2018 | Maruyama | H04N 5/142 |
| 2018/0330529 A1* | 11/2018 | Maruyama | G06T 7/90 |
| 2018/0344136 A1 | 12/2018 | Kikuchi | |
| 2019/0082094 A1* | 3/2019 | Endo | A61B 1/00009 |
| 2019/0124258 A1* | 4/2019 | Ioka | A61B 1/00009 |
| 2019/0231178 A1 | 8/2019 | Kikuchi | |
| 2019/0335979 A1 | 11/2019 | Moriya | |
| 2020/0305700 A1* | 10/2020 | Kamon | A61B 1/0646 |

FOREIGN PATENT DOCUMENTS

| | | |
|---|---|---|
| JP | 2009284959 A | 12/2009 |
| JP | 2012040169 A | 3/2012 |
| JP | 2015116328 A | 6/2015 |
| JP | 5925169 B2 | 4/2016 |

OTHER PUBLICATIONS

Written Opinion dated Dec. 12, 2017 issued in International Application No. PCT/JP2017/036189.

Japanese Office Action (and English language translation thereof) dated Nov. 17, 2020 issued in Japanese Application No. 2019-546475.

* cited by examiner

ENDOSCOPE DEVICE, IMAGE PROCESSING METHOD, AND COMPUTER READABLE RECORDING MEDIUM

CROSS-REFERENCE TO RELATED APPLICATION

This application is a continuation of International Application No. PCT/JP2017/036189, filed on Oct. 4, 2017, the entire contents of which are incorporated herein by reference.

BACKGROUND

1. Technical Field

The present disclosure relates to an endoscope device, an image processing method, and a computer-readable recording medium.

2. Related Art

In the related art, in a medical field and an industrial field, an endoscope device is widely used in order for various examinations. In particular, a medical endoscope device has been in widespread use since an elongated flexible insertion portion in which an image sensor including a plurality of pixels is provided on a distal end is inserted into the body cavity of a subject such as a patient, and thus, an in-vivo image in the body cavity can be acquired without incising the subject, and a load on the subject is small.

Sequential lighting of acquiring color information by emitting an illumination in a wavelength band different for each frame, and simultaneous lighting of acquiring the color information by a color filter provided on the image sensor are used as an imaging mode of the endoscope device. In the sequential lighting, color separation performance and resolution are excellent, but a color shift occurs in a dynamic scene. In contrast, in the simultaneous lighting, the color shift does not occur, but the color separation performance and the resolution are degraded compared to the sequential lighting.

In addition, a white light observation mode (white light imaging: WLI) using white illumination light (white light) and a narrowband light observation mode (narrow band imaging: NBI) using illumination light (narrowband light) including two narrowband light rays that are respectively included in a blue wavelength band and a green wavelength band are widely known as an observation mode of the endoscope device of the related art. In the white light observation mode, a color image is generated by using a signal of the green wavelength band as a luminance signal, and in the narrowband light observation mode, a pseudo color image is generated by using a signal of the blue wavelength band as a luminance signal. In particular, in the narrowband light observation mode, it is possible to obtain an image in which a capillary blood vessel, a mucosa fine pattern, and the like existing in the superficial portion of the mucosa of a living body are enhanced and displayed. According to the narrowband light observation mode, it is possible to more accurately detect an affected area in the superficial portion of the mucosa of the living body. In such an observation mode of the endoscope device, it is also known that the observation is performed by switching between the white light observation mode and the narrowband light observation mode.

In order to generate and display the color image in the observation mode described above, in general, a color filter referred to as a Bayer array is provided on a light receiving surface of the image sensor such that a captured image is acquired by an image sensor of a single plate. In this case, each of the pixels receives light in a wavelength band that is transmitted through the filter, and generates an electric signal of a color component according to the light in the wavelength band. For this reason, in processing of generating the color image, interpolation processing of interpolating a signal value of a missing color component that is not transmitted through the filter in each of the pixels is performed. Such interpolation processing is referred to as demosaicing processing. In addition, in general, the color filter referred to as the Bayer array is provided on the light receiving surface of the image sensor. In the Bayer array, filters transmitting light in a red (R) wavelength band, a green (G) wavelength band, and a blue (B) wavelength band (hereinafter, referred to as an "R filter", a "G filter", and a "B filter") are arranged in each of the pixels, as one filter unit.

Recently, in order to obtain high sense of resolution in any of the white light observation mode and the narrowband light observation mode, in the living body, a technology of disposing not only a primary color filter but also a complementary color filter of cyan (Cy) or magenta (Mg) (hereinafter, referred to as a "Cy filter" and an "Mg filter") to be mixed is known (JP 2015-116328 A). According to such a technology, it is possible to acquire more information of the blue wavelength band by mixing a complementary pixel, compared to a case where only a primary pixel is provided, and thus, in the case of the narrowband light observation mode, it is possible to improve the resolution of the capillary blood vessel or the like.

SUMMARY

In some embodiments, an endoscope device includes: a light source configured to perform any one of simultaneous lighting and sequential lighting, the simultaneous lighting being simultaneously emitting a plurality of light rays of which at least wavelength bands are different from each other, the sequential lighting being individually emitting a plurality of light rays of which at least wavelength bands are different from each other; an image sensor including a plurality of pixels disposed into a shape of a two-dimensional lattice, each pixel being configured to generate an imaging signal by receiving light and by performing photoelectric conversion; a plurality of filters including at least one type of primary filter and a complementary filter, the at least one type of primary filter being configured to transmit light in any one wavelength band of a red wavelength band, a green wavelength band, and a blue wavelength band, the complementary filter being configured to transmit light in the green wavelength band and transmits light in one wavelength band of the red wavelength band and the blue wavelength band, each of the plurality of filters being disposed to correspond to each of the plurality of pixels; and a processor including hardware, the processor being configured to cause the light source to switch between the simultaneous lighting and the sequential lighting, when the simultaneous lighting is performed, perform interpolation processing to generate an output image by using an imaging signal generated from a pixel corresponding to the complementary filter, and when the sequential lighting is performed, perform interpolation processing to generate an output image by using an imaging signal generated from a pixel corresponding to the complementary filter as an imaging signal generated from a pixel corresponding to the at least one type of primary filter.

In some embodiments, provides is an image processing method executed by an endoscope device including: a light source configured to perform any one of simultaneous lighting and sequential lighting, the simultaneous lighting being simultaneously emitting a plurality of light rays of which at least wavelength bands are different from each other, the sequential lighting being individually emitting a plurality of light rays of which at least wavelength bands are different from each other; an image sensor including a plurality of pixels disposed into a shape of a two-dimensional lattice, each pixel being configured to generate an imaging signal by receiving light and by performing photoelectric conversion; and a plurality of filters including at least one type of primary filter and a complementary filter, the at least one type of primary filter being configured to transmit light in any one wavelength band of a red wavelength band, a green wavelength band, and a blue wavelength band, the complementary filter being configured to transmit light in the green wavelength band and transmits light in one wavelength band of the red wavelength band and the blue wavelength band, each of the plurality of filters being disposed to correspond to each of the plurality of pixels. The method includes: switching between the simultaneous lighting and the sequential lighting, with respect to the light source; when the simultaneous lighting is performed, performing interpolation processing to generate an output image by using an imaging signal generated from a pixel corresponding to the complementary filter; and when the sequential lighting is performed, performing interpolation processing to generate an output image by using an imaging signal generated from a pixel corresponding to the complementary filter as an imaging signal generated from a pixel corresponding to the at least one type of primary filter.

In some embodiments, provided is a non-transitory computer-readable recording medium in which an executable program is recorded. The program causes an endoscope device including: a light source configured to perform any one of simultaneous lighting and sequential lighting, the simultaneous lighting being simultaneously emitting a plurality of light rays of which at least wavelength bands are different from each other, the sequential lighting being individually emitting a plurality of light rays of which at least wavelength bands are different from each other; an image sensor including a plurality of pixels disposed into a shape of a two-dimensional lattice, each pixel being configured to generate an imaging signal by receiving light and by performing photoelectric conversion; and a plurality of filters including at least one type of primary filter and a complementary filter, the at least one type of primary filter being configured to transmit light in any one wavelength band of a red wavelength band, a green wavelength band, and a blue wavelength band, the complementary filter being configured to transmit light in the green wavelength band and transmits light in one wavelength band of the red wavelength band and the blue wavelength band, each of the plurality of filters being disposed to correspond to each of the plurality of pixels, to execute: switching between the simultaneous lighting and the sequential lighting, with respect to the light source; when the simultaneous lighting is performed, performing interpolation processing to generate an output image by using an imaging signal generated from a pixel corresponding to the complementary filter; and when the sequential lighting is performed, performing interpolation processing to generate an output image by using an imaging signal generated from a pixel corresponding to the complementary filter as an imaging signal generated from a pixel corresponding to the at least one type of primary filter.

The above and other features, advantages and technical and industrial significance of this disclosure will be better understood by reading the following detailed description of presently preferred embodiments of the disclosure, when considered in connection with the accompanying drawings.

DETAILED DESCRIPTION

Figure 1:
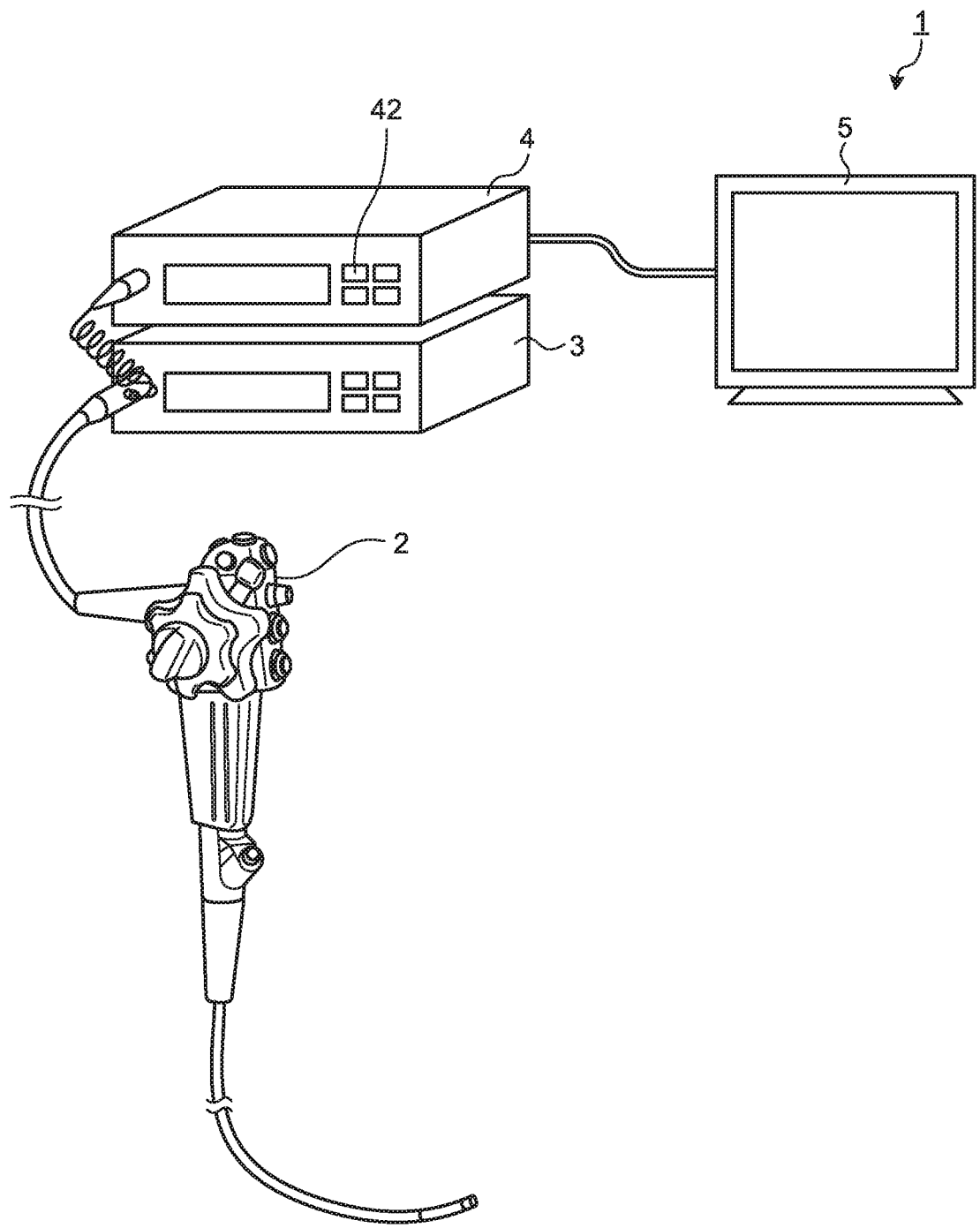
FIG. 1 is a diagram illustrating a schematic configuration of an endoscope device according to a first embodiment of the disclosure.

Hereinafter, modes for carrying out the disclosure (hereinafter, referred to as "embodiments") will be described. In the embodiments, a medical endoscope device will be described in which an image of the inside of the body cavity of a subject such as a patient is captured and displayed. In addition, the disclosure is not limited to the embodiments. Further, in the description of the drawings, the same reference numerals are applied to the same portions.

First Embodiment

Configuration of Endoscope Device

Figure 2:
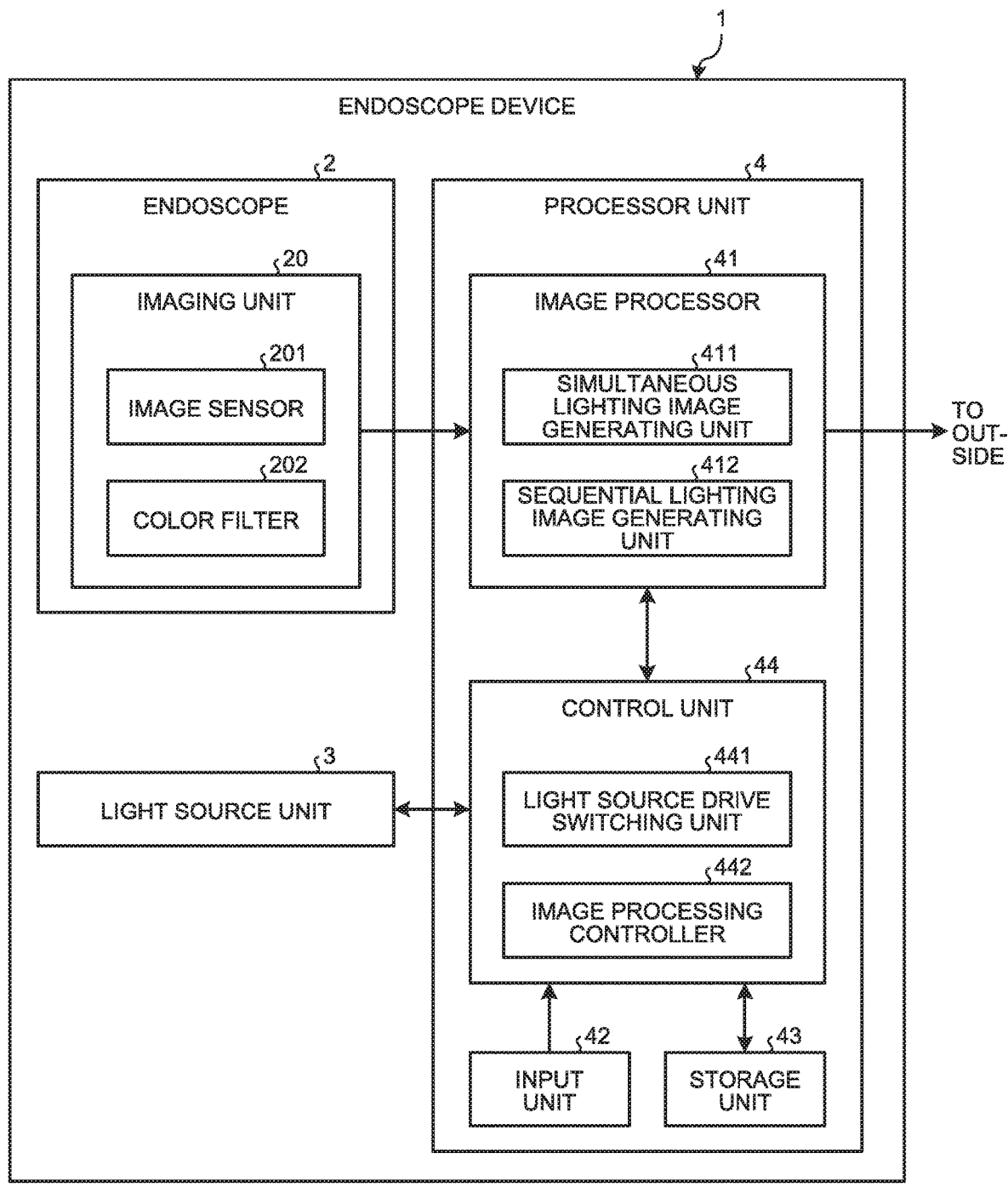
FIG. 2 is a block diagram schematically illustrating a function configuration of the endoscope device according to the first embodiment of the disclosure.

FIG. 1 is a diagram illustrating a schematic configuration of an endoscope device according to a first embodiment of the disclosure. FIG. 2 is a block diagram schematically illustrating a function configuration of the endoscope device according to the first embodiment of the disclosure. An endoscope device 1 illustrated in FIG. 1 and FIG. 2 is inserted into a subject such as a patient, captures the inside of the subject, and outputs an in-vivo image to a display device on the outside. A user such as a medical doctor examines the presence or absence of each of a bleeding site, a tumor site, and an abnormal site that are a site to be detected, by observing the in-vivo image that is displayed on the display device.

The endoscope device 1 includes an endoscope 2 that is inserted into the subject, and thus, captures an in-vivo image of an observed region, and generates an imaging signal, a light source unit 3 that generates illumination light exiting from a distal end of the endoscope 2, a processor unit 4 that performs predetermined image processing with respect to the imaging signal generated by the endoscope 2, and comprehensively controls the overall operation of the endoscope device 1, and a display unit 5 that displays the in-vivo image subjected to the image processing by the processor unit 4.

The endoscope 2 includes an imaging unit 20 that generates at least the imaging signal. The imaging unit 20 includes an image sensor 201 that generates an imaging signal by disposing pixels (photodiodes) receiving light into the shape of a two-dimensional matrix, and by performing photoelectric conversion with respect to the light received in each of the pixels, and a color filter 202 that is disposed on a light receiving surface of the image sensor 201, and includes a plurality of filters individually transmitting light in a set wavelength band. The image sensor 201 is attained by using an image sensor such as a complementary metal oxide semiconductor (CMOS) or a charge coupled device (CCD). Note that, the detailed configuration of the image sensor 201 and the color filter 202 will be described below.

The light source unit 3 emits illumination light in simultaneous lighting of simultaneously emitting a plurality of light rays of which at least wavelength bands are different from each other and sequential lighting of individually (in a time-division manner) emitting the plurality of light rays of which at least the wavelength bands are different from each other, under the control of the processor unit 4. Specifically, the light source unit 3 emits the illumination light in the simultaneous lighting of simultaneously emitting two types of light rays of which at least wavelength bands are different from each other, or emits the illumination light in the sequential lighting of alternately emitting two types of light rays of which at least the wavelength bands are different from each other. The light source unit 3 is configured by using a plurality of light sources, for example, a red light emitting diode (LED) lamp generating light in a red wavelength band, a green LED lamp generating light in a green wavelength band, and a blue LED lamp generating light in a blue wavelength band.

The processor unit 4 includes an image processor 41 that performs the image processing with respect to the imaging signal input from the imaging unit 20, generates an output image, and outputs the image to the display unit 5, an input unit 42 that receives the input of an instruction signal for giving an instruction on various operations, a storage unit 43 that stores various programs to be executed by the endoscope device 1, data in processing, and the like, and a control unit 44 that comprehensively controls each unit configuring the endoscope device 1.

The image processor 41 is configured by using a graphics processing unit (GPU) or the like. The image processor 41 includes a simultaneous lighting image generating unit 411 that performs interpolation processing with respect to the imaging signal generated by the imaging unit 20, and generates the output image in a case where the light source unit 3 emits the illumination light in the simultaneous lighting, and a sequential lighting image generating unit 412 that performs the interpolation processing with respect to the imaging signal generated by the imaging unit 20, and generates the output image in a case where the light source unit 3 emits the illumination light in the sequential lighting.

The input unit 42 is configured by using a switch, a button, a touch panel, and the like, receives the input of the instruction signal for giving an instruction on the operation of the endoscope device 1, and outputs the received instruction signal to the control unit 44. Specifically, the input unit 42 receives the input of an instruction signal for switching the mode of the illumination light that is emitted from the light source unit 3. For example, in a case where the light source unit 3 emits the illumination light in the simultaneous lighting, the input unit 42 receives the input of an instruction signal for allowing the light source unit 3 to emit the illumination light in the sequential lighting.

The storage unit 43 is configured by using a volatile memory or a non-volatile memory, and stores various information items relevant to the endoscope device 1 or a program that is executed by the endoscope device 1.

The control unit 44 is configured by using a central processing unit (CPU). The control unit 44 includes a light source drive switching unit 441 that switches the mode of the illumination light emitted from the light source unit 3, on the basis of the instruction signal for switching the mode of the illumination light emitted from the light source unit 3, the instruction signal being input from the input unit 42, and an image processing controller 442 that switches an interpolation processing method of the image processor 41, on the basis of the mode of the light source unit 3 that is switched by the light source drive switching unit 441.

The display unit 5 receives an output image signal generated by the processor unit 4 through a video cable, and displays an in-vivo image corresponding to the output image signal. The display unit 5 is configured by using a liquid crystal or organic electro luminescence (EL).

Configuration of Image Sensor

Figure 3:
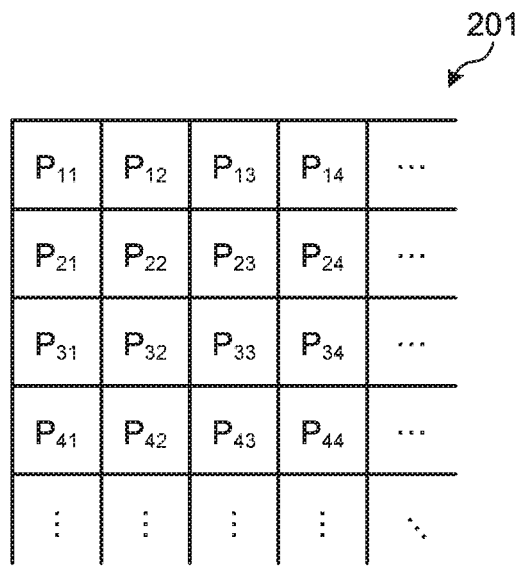
FIG. 3 is a schematic diagram illustrating a configuration of a pixel of an image sensor according to the first embodiment of the disclosure.

Next, the detailed configuration of the image sensor 201 will be described. FIG. 3 is a schematic diagram illustrating the configuration of the pixel of the image sensor 201.

As illustrated in FIG. 3, in the image sensor 201, a plurality of pixels P receiving light are disposed into the shape of a two-dimensional lattice (a two-dimensional matrix). Each of the pixels P generates the imaging signal by receiving light incident from an imaging optical system 200, and by performing the photoelectric conversion. In the imaging signal, a luminance value (a pixel value) of each of the pixels P, position information of the pixel, and the like are included. In FIG. 3, a pixel that is disposed in the i-th row and the j-th column is represented as a pixel $P_{ij}$. Note that, i and j are an integer of greater than or equal to 1.

Configuration of Color Filter

Figure 4:
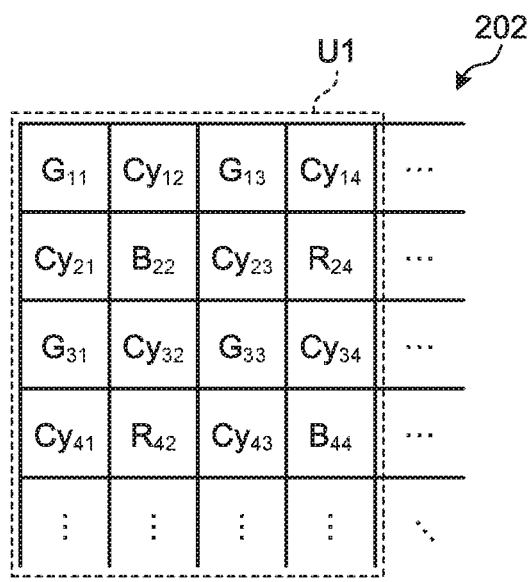
FIG. 4 is a schematic diagram illustrating an example of a configuration of a color filter according to the first embodiment of the disclosure.

Next, the detailed configuration of the color filter 202 will be described. FIG. 4 is a schematic diagram illustrating an example of the configuration of the color filter 202.

As illustrated in FIG. 4, in the color filter 202, a filter unit U1 including 16 filters arranged into the shape of a two-dimensional lattice of 4×4 is disposed in accordance with the disposition of the pixel $P_{ij}$. The pixel $P_{ij}$ in which the filter is provided receives light in a wavelength band that is transmitted through the filter. Specifically, the pixel $P_{ij}$ in which a filter R transmitting light in a red wavelength band is provided receives the light in the red wavelength band. Hereinafter, the pixel $P_{ij}$ receiving the light in the red wavelength band will be referred to as an R pixel. Similarly, the pixel $P_{ij}$ receiving light in a green wavelength band will be referred to as a G pixel, the pixel $P_{ij}$ receiving light in a blue wavelength band will be referred to as a B pixel, and the pixel $P_{ij}$ receiving the light in the green wavelength band and the light in the blue wavelength band will be referred to as a Cy pixel. Note that, hereinafter, the R pixel, the G pixel, and the B pixel will be described as a primary pixel, and the Cy pixel will be described as a complementary pixel.

As illustrated in FIG. 4, the filter unit U1 transmits light in a blue (B) wavelength band $H_B$, in a green (G) wavelength band $H_G$, and in a red (R) wavelength band $H_R$. Here, in the blue, green, and red wavelength bands $H_B$, $H_G$, and $H_R$, the wavelength band $H_B$ is 390 nm to 500 nm, the wavelength band $H_G$ is 500 nm to 600 nm, and the wavelength band $H_R$ is 600 nm to 700 nm. In addition, the filter unit U1 includes an R filter transmitting the light in the red wavelength band $H_R$, a G filter transmitting the light in the green wavelength band $H_G$, a B filter transmitting the light in the blue wavelength band $H_B$, and a Cy filter transmitting the light in the blue wavelength band and the light in the green wavelength band. Specifically, in the filter unit U1, the Cy filter is disposed into the shape of a check at a ratio of 1/2 to the whole (eight Cy filters), the G filter is disposed at a ratio of 1/4 to the whole (four G filters), and each of the B filter and the R filter is disposed at a ratio of 1/8 (two B filters and two R filters).

Transmission Properties of Each Filter

Figure 5:
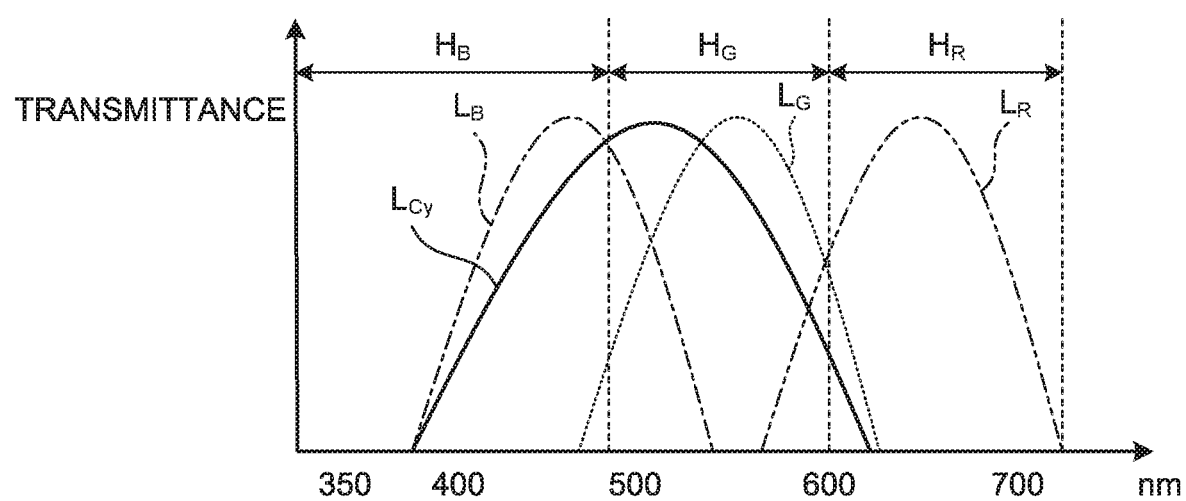
FIG. 5 is a diagram illustrating an example of transmission properties of each filter configuring the color filter according to the first embodiment of the disclosure.

Next, transmission properties of each of the filters configuring the color filter 202 will be described. FIG. 5 is a diagram illustrating an example of the transmission properties of each of the filters configuring the color filter 202. In FIG. 5, a transmittance curve is simulatively standardized such that the maximum values of the transmittances of each of the filters are identical to each other. In FIG. 5, a curve $L_B$ represents a transmittance curve of the B filter, a curve LG represents a transmittance curve of the G filter, a curve $L_R$ represents a transmittance curve of the R filter, and a curve $L_{Cy}$ represents a transmittance curve of the Cy filter. In addition, in FIG. 5, a horizontal axis represents a wavelength, and a vertical axis represents a transmittance.

As illustrated in FIG. 5, the B filter transmits the light in the wavelength band $H_B$. The Cy filter transmits the light in each of the wavelength band $H_B$ and the wavelength band $H_G$, and absorbs (shields) the light in the wavelength band $H_R$. That is, the Cy filter transmits light in a wavelength band of cyan that is a complementary color. The G filter transmits the light in the wavelength band $H_G$. The R filter transmits the light in the wavelength band $H_R$. Note that, herein, the complementary color indicates a color that is configured by light including at least two wavelength bands of the wavelength bands $H_B$, $H_G$, and $H_R$.

In the endoscope device 1 configured as described above, the endoscope 2 captures a subject irradiated with the illumination light by the light source unit 3 through the endoscope 2, and the processor unit 4 performs various signal processings with respect to the imaging signal generated by the endoscope 2, and thus, the color image is generated and is displayed on the display unit 5. In such a case, in a case where an instruction signal for giving an instruction on the simultaneous lighting is input from the input unit 42, the light source drive switching unit 441 allows the light source unit 3 to emit the illumination light in the simultaneous lighting, and in a case where an instruction signal for giving an instruction on the sequential lighting is input from the input unit 42, the light source drive switching unit 441 allows the light source unit 3 to emit the illumination light in the sequential lighting. At this time, the image processing controller 442 switches the interpolation processing method of the image processor 41, on the basis of the mode of the light source unit 3 that is switched by the light source drive switching unit 441. Specifically, in a case where the mode of the light source unit 3 is the simultaneous lighting, the image processing controller 442 allows the simultaneous lighting image generating unit 411 to perform the interpolation processing with respect to the imaging signal generated by the imaging unit 20, and to generate the output image to be output to the display unit 5, and in a case where the mode of the light source unit 3 is the sequential lighting, the image processing controller 442 allows the sequential lighting image generating unit 412 to execute the interpolation processing with respect to the imaging signal generated by the imaging unit 20, and to generate the output image to be output to the display unit 5.

According to the first embodiment of the disclosure described above, in a case where the mode of the light source unit 3 is the simultaneous lighting, the image processing controller 442 allows the simultaneous lighting image generating unit 411 to perform the interpolation processing with respect to the imaging signal generated by the imaging unit 20, and to generate the output image to be output to the display unit 5, and in a case where the mode of the light source unit 3 is the sequential lighting, the image processing controller 442 allows the sequential lighting image generating unit 412 to execute the interpolation processing with respect to the imaging signal generated by the imaging unit 20, and to generate the output image to be output to the display unit 5, and thus, even in a case where the imaging is performed by using the image sensor 201 provided with the color filter 202 in which the primary pixel and the complementary pixel are mixed, it is possible to generate an output image without a color shift that is captured in the simultaneous lighting and an output image excellent in color separation and resolution that is captured in the sequential lighting.

Second Embodiment

Next, a second embodiment of the disclosure will be described. The second embodiment is different from the first embodiment described above in the configuration and the processing. Hereinafter, the configuration of an endoscope device according to the second embodiment will be described, and then, processing that is executed by the endoscope device will be described. Note that, the same reference numerals will be applied to the same configurations as those of the endoscope device 1 according to the first embodiment described above, and the detailed description thereof will be omitted.

Configuration of Endoscope Device

Figure 6:
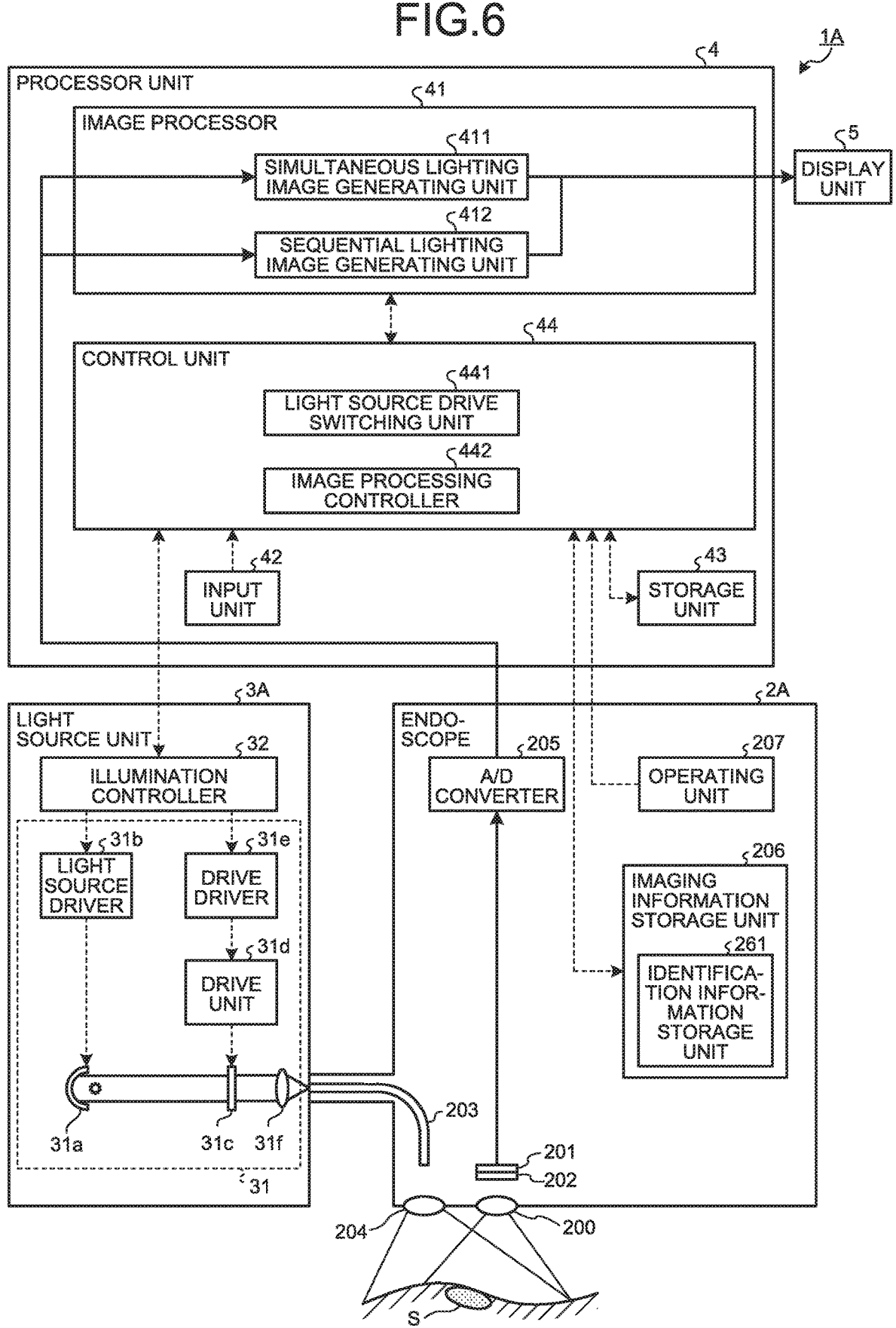
FIG. 6 is a schematic diagram illustrating a schematic configuration of an endoscope device according to a second embodiment of the disclosure.

FIG. 6 is a schematic diagram illustrating a schematic configuration of the endoscope device according to the second embodiment of the disclosure. An endoscope device 1A illustrated in FIG. 6 includes an endoscope 2A that is inserted into the subject, and thus, captures an in-vivo image of the observed region, and generates an imaging signal, a light source unit 3A that generates illumination light exiting from a distal end of the endoscope 2A, the processor unit 4, and the display unit 5. A user such as a medical doctor examines the presence or absence of each of a bleeding site, a tumor site (an affected area S), and an abnormal site that are a site to be detected, by observing the in-vivo image that is displayed on the display unit 5.

Configuration of Endoscope

First, the configuration of the endoscope 2A will be described.

The endoscope 2A includes an imaging optical system 200, an image sensor 201, a color filter 202, a light guide 203, an illumination lens 204, an A/D converter 205, an imaging information storage unit 206, and an operating unit 207.

The imaging optical system 200 condenses light from at least the observed region. The imaging optical system 200 is configured by one or a plurality of lenses. Note that, in the imaging optical system 200, an optical zoom mechanism that changes the angle of view and a focus mechanism that changes a focal point may be provided.

The light guide 203 is configured by using fiberglass or the like, and forms a light guide path of light exiting from the light source unit 3A.

The illumination lens 204 is provided on a distal end of the light guide 203, and diffuses light that is guided by the light guide 203 to exit to the outside from the distal end of the endoscope 2A. The illumination lens 204 is configured by using one or a plurality of lenses.

The A/D converter 205 performs A/D conversion with respect to an analog imaging signal that is generated by the image sensor 201, and outputs a digital imaging signal that is converted to the processor unit 4.

The imaging information storage unit 206 stores data including various program items for operating the endoscope 2A, various parameters necessary for operating the endoscope 2A, and identification information of the endoscope 2A. In addition, the imaging information storage unit 206 includes an identification information storage unit 261 in which the identification information is recorded. In the identification information, unique information (ID), a model year, specification information, and a transmission mode of the endoscope 2A, filter arrangement information of the color filter 202, and the like are included. The imaging information storage unit 206 is attained by using a flash memory or the like.

The operating unit 207 receives the input of an instruction signal for switching the operation of the endoscope 2A, an instruction signal for allowing the light source unit 3A to perform a switching operation with respect to the illumination light, or the like, and outputs the received instruction signal to the processor unit 4. The operating unit 207 is configured by using a switch, a jog dial, a button, a touch panel, and the like.

Configuration of Light Source Unit

Next, the configuration of the light source unit 3A will be described. The light source unit 3A includes an illumination unit 31 and an illumination controller 32.

The illumination unit 31 allows illumination light rays of which wavelength bands are different from each other to exit to the light guide 203, under the control of the illumination controller 32. The illumination unit 31 includes a light source 31a, a light source driver 31b, a switching filter 31c, a drive unit 31d, and a drive driver 31e.

The light source 31a allows the illumination light to exit, under the control of the illumination controller 32. The illumination light exiting from the light source 31a exits to the outside from the distal end of the endoscope 2A through the switching filter 31c, a condenser lens 31f, and the light guide 203. The light source 31a is attained by using a plurality of LED lamps or a plurality of laser light sources emitting light rays of which wavelength bands are different from each other. Specifically, the light source 31a is configured by using three LED lamps of an LED 31a_B, an LED 31a_G, and an LED 31a_R.

Figure 7:
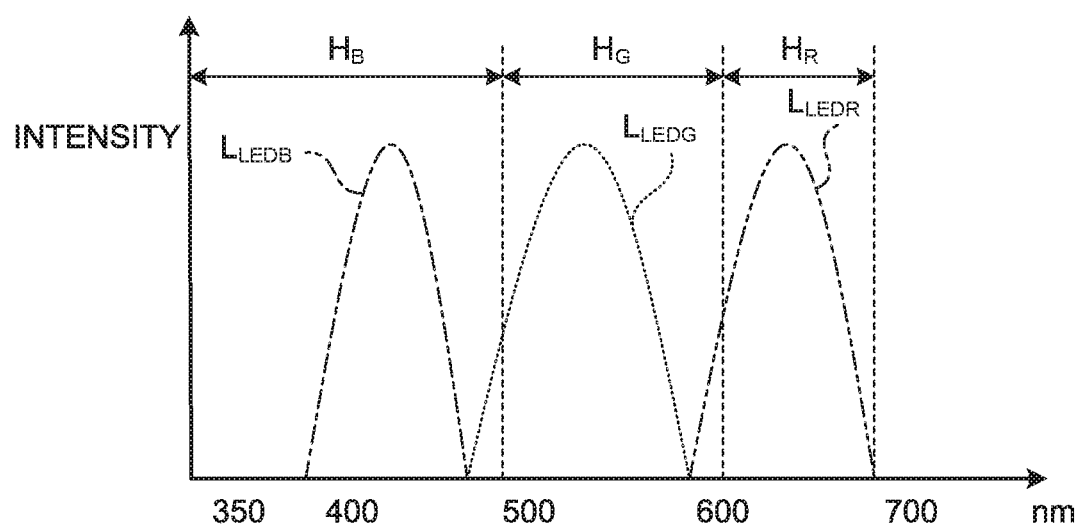
FIG. 7 is a diagram illustrating an example of spectroscopic properties of each light ray that exits from a light source unit according to the second embodiment of the disclosure.

FIG. 7 is a diagram illustrating an example of spectroscopic properties of each light ray that exits from the light source 31a. In FIG. 7, a horizontal axis represents a wavelength, and a vertical axis represents an intensity. In FIG. 7, a curve $L_{LEDB}$ represents spectroscopic properties of blue illumination light that is emitted by the LED 31a_B, a curve $L_{LEDG}$ represents spectroscopic properties of green illumination light that is emitted by the LED 31a_G, and a curve $L_{LEDR}$ represents spectroscopic properties of red illumination light that is emitted by the LED 31a_R.

As illustrated in the curve $L_{LEDB}$ of FIG. 7, the LED 31a_B has a peak intensity in the blue wavelength band $H_B$ (for example, 380 nm to 480 nm). In addition, as illustrated in the curve $L_{LEDG}$ of FIG. 7, the LED 31a_G has a peak intensity in the green wavelength band $H_G$ (for example, 480 nm to 580 nm). Further, as illustrated in the curve $L_{LEDR}$ of FIG. 7, the LED 31a_R has a peak intensity in the red wavelength band $H_R$ (for example, 580 nm to 680 nm).

Returning to FIG. 6, the configuration of the endoscope device 1A will be continuously described.

The light source driver 31b supplies a current to the light source 31a, under the control of the illumination controller 32, and thus, allows the illumination light to exit to the light source 31a.

The switching filter 31c is disposed to be removably inserted onto a light path of the illumination light exiting from the light source 31a, and transmits light in a predetermined wavelength band, in the illumination light exiting from the light source 31a. Specifically, the switching filter 31c transmits the blue narrowband light and the green narrowband light. That is, in a case where the switching filter 31c is disposed on the light path of the illumination light, two narrowband light rays are transmitted. More specifically, the switching filter 31c transmits light in a narrowband $T_B$ that is included in the wavelength band $H_B$ (for example, 390 nm to 445 nm) and light in a narrowband $T_G$ that is included in the wavelength band $H_G$ (for example, 530 nm to 550 nm).

Figure 8:
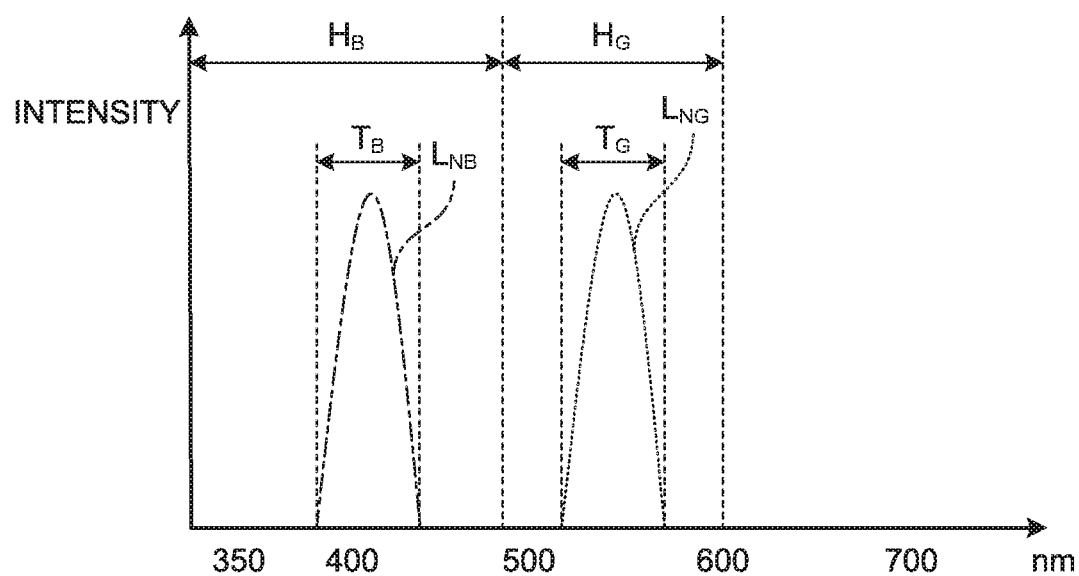
FIG. 8 is a diagram illustrating an example of spectroscopic properties of narrowband light that exits from the light source unit according to the second embodiment of the disclosure.

FIG. 8 is a diagram illustrating an example of spectroscopic properties of narrowband light that exits from the light source unit 3A. In FIG. 8, a horizontal axis represents a wavelength, and a vertical axis represents an intensity. In addition, in FIG. 8, a curve $L_{NB}$ represents spectroscopic properties of narrowband light in the narrowband $T_B$ that is transmitted through the switching filter 31c, and a curve $L_{NG}$ represents spectroscopic properties of narrowband light in the narrowband $T_G$ that is transmitted through the switching filter 31c.

As illustrated in the curve $L_{NB}$ and the curve $L_{NG}$ of FIG. 8, the switching filter 31c transmits the light in the blue narrowband $T_B$ and the light in the green narrowband $T_G$. The light that is transmitted through the switching filter 31c is narrowband illumination light in the narrowband $T_B$ and the narrowband $T_G$. The narrowbands $T_B$ and $T_G$ are a wavelength band of the blue light and the green light that are easily absorbed in hemoglobin in the blood. Image observation of the narrowband illumination light is referred to as a narrowband light observation mode (an NBI mode).

Returning to FIG. 6, the configuration of the endoscope device 1A will be continuously described.

The drive unit 31d is configured by using a stepping motor, a DC motor, or the like, and inserts the switching filter 31c onto the light path of the illumination light exiting from the light source 31a or retracts the switching filter 31c from the light path, under the control of the illumination controller 32. Specifically, in a case where endoscope device 1A performs a white light observation mode (a WLI mode), the drive unit 31d retracts the switching filter 31c from the light path of the illumination light exiting from the light source 31a, and in a case where the endoscope device 1A performs the narrowband light observation mode (the NBI mode), the drive unit 31d inserts (disposes) the switching filter 31c onto the light path of the illumination light exiting from the light source 31a, under the control of the illumination controller 32.

The drive driver 31e supplies a predetermined current to the drive unit 31d, under the control of the illumination controller 32.

The condenser lens 31f condenses the illumination light that is emitted from the light source 31a to exit to the light guide 203. In addition, the condenser lens 31f condenses the illumination light that is transmitted through the switching filter 31c to exit to the light guide 203. The condenser lens 31f is configured by using one or a plurality of lenses.

The illumination controller 32 is configured by using a CPU or the like. The illumination controller 32 controls the light source driver 31b such that the light source 31a is turned on and off, on the basis of the instruction signal that is input from the processor unit 4. In addition, the illumination controller 32 controls the type (band) of illumination light exiting from the illumination unit 31 by controlling the drive driver 31e, and by inserting the switching filter 31c onto the light path of the illumination light exiting from the light source 31a or retracting the switching filter 31c from the light path, on the basis of the instruction signal that is input from the processor unit 4. Specifically, in the case of the sequential lighting, the illumination controller 32 individually turns on at least two LED lamps of the light source 31a, and in the case of the simultaneous lighting, the illumination controller 32 simultaneously turns on at least two LED lamps of the light source 31a, and thus, control of switching the mode of the illumination light exiting from the illumination unit 31 to any one of the sequential lighting and the simultaneous lighting is performed.

Lighting Control of Illumination Unit by Illumination Controller

Next, lighting control of the illumination unit 31 by the illumination controller 32 will be described.

Figure 9:
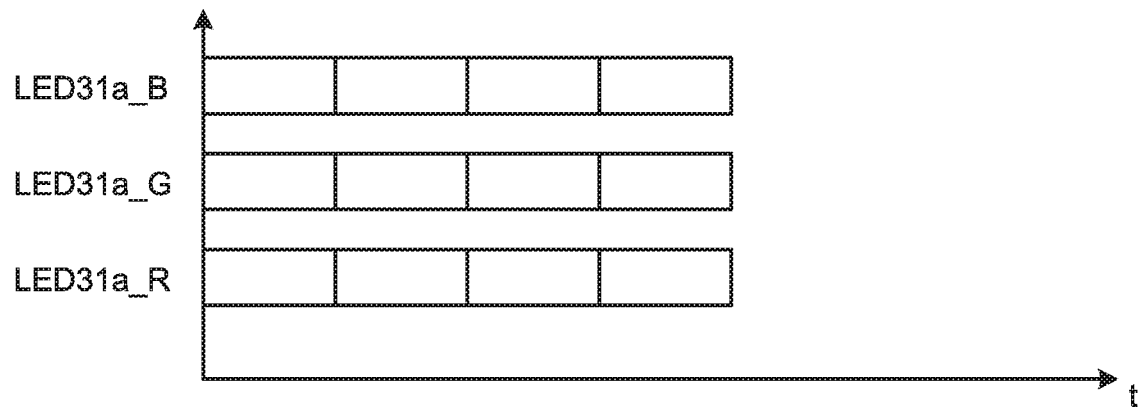
FIG. 9 is a diagram schematically illustrating lighting control of an illumination unit that is performed by an illumination controller according to the second embodiment of the disclosure, at the time of white light observation of simultaneous lighting.
Figure 10:
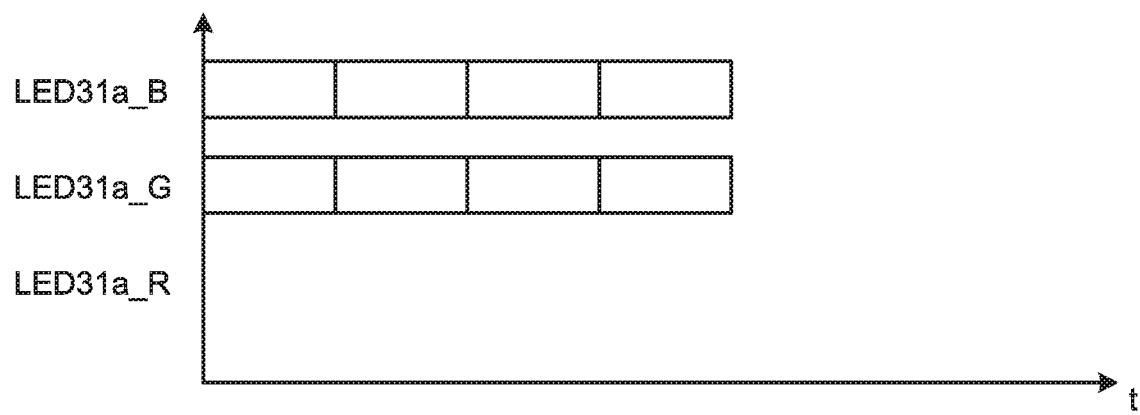
FIG. 10 is a diagram schematically illustrating the lighting control of the illumination unit that is performed by the illumination controller according to the second embodiment of the disclosure, at the time of narrowband light observation of the simultaneous lighting.
Figure 11:
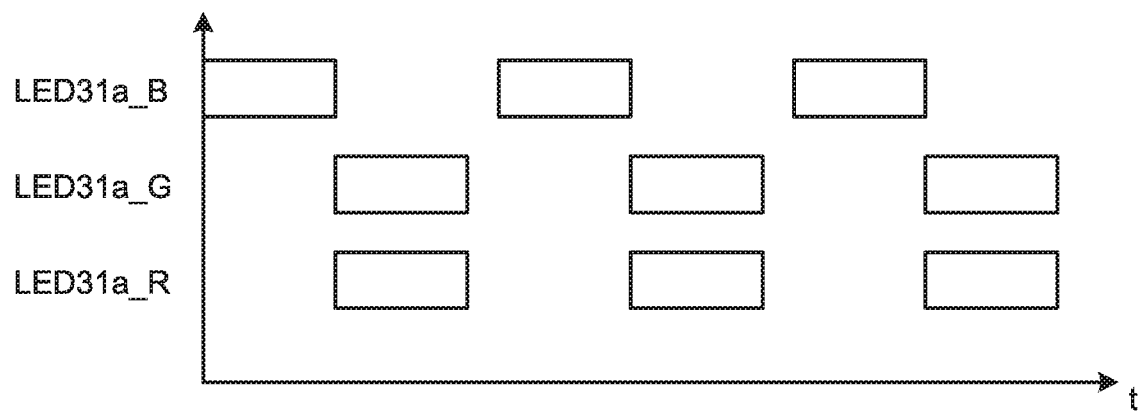
FIG. 11 is a diagram schematically illustrating the lighting control of the illumination unit that is performed by the illumination controller according to the second embodiment of the disclosure, at the time of the white light observation of sequential lighting.
Figure 12:
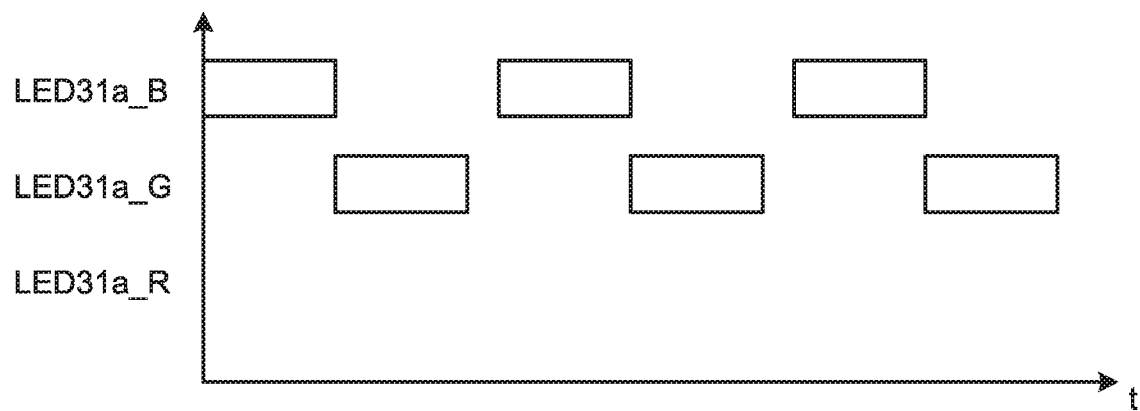
FIG. 12 is a diagram schematically illustrating the lighting control of the illumination unit that is performed by the illumination controller according to the second embodiment of the disclosure, at the time of the narrowband light observation of the sequential lighting.

FIG. 9 is a diagram schematically illustrating the lighting control of the illumination unit 31 that is performed by the illumination controller 32, at the time of white light observation of the simultaneous lighting. FIG. 10 is a diagram schematically illustrating the lighting control of the illumination unit 31 that is performed by the illumination controller 32, at the time of narrowband light observation of the simultaneous lighting. FIG. 11 is a diagram schematically illustrating the lighting control of the illumination unit 31 that is performed by the illumination controller 32, at the time of the white light observation of the sequential lighting. FIG. 12 is a diagram schematically illustrating the lighting control of the illumination unit 31 that is performed by the illumination controller 32, at the time of the narrowband light observation of the sequential lighting. In FIG. 9 to FIG. 12, a horizontal axis represents time, and a vertical axis represents a lighting timing of each of the LEDs.

As illustrated in FIG. 9, in a case where the endoscope device 1A performs the white light observation of the simultaneous lighting, the illumination controller 32 simultaneously turns on the LED 31a_B, the LED 31a_G, and the LED 31a_R at a predetermined interval. In addition, as illustrated in FIG. 10, in a case where the endoscope device 1A performs the narrowband light observation of the simultaneous lighting, the illumination controller 32 simultaneously turns on the LED 31a_B and the LED 31a_G at a predetermined interval.

As illustrated in FIG. 11, in a case where the endoscope device 1A performs the white light observation of the sequential lighting, the illumination controller 32 turns on each of the LED 31a_B, the LED 31a_G, and the LED 31a_R at an individual timing by alternately repeating a first period in which only the LED 31a_B is turned on and a second period in which the LED 31a_G and the LED 31a_R are turned on. In addition, as illustrated in FIG. 12, in a case where the endoscope device 1A performs the narrowband light observation of the sequential lighting, the illumination controller 32 turns on each of the LED 31a B and the LED 31a_G at an individual timing by alternately repeating a first period in which only the LED 31a_B is turned on and a second period in which only the LED 31a_G is turned on.

Processing of Endoscope Device

Next, processing that is executed by the endoscope device 1A will be described.

Figure 13:
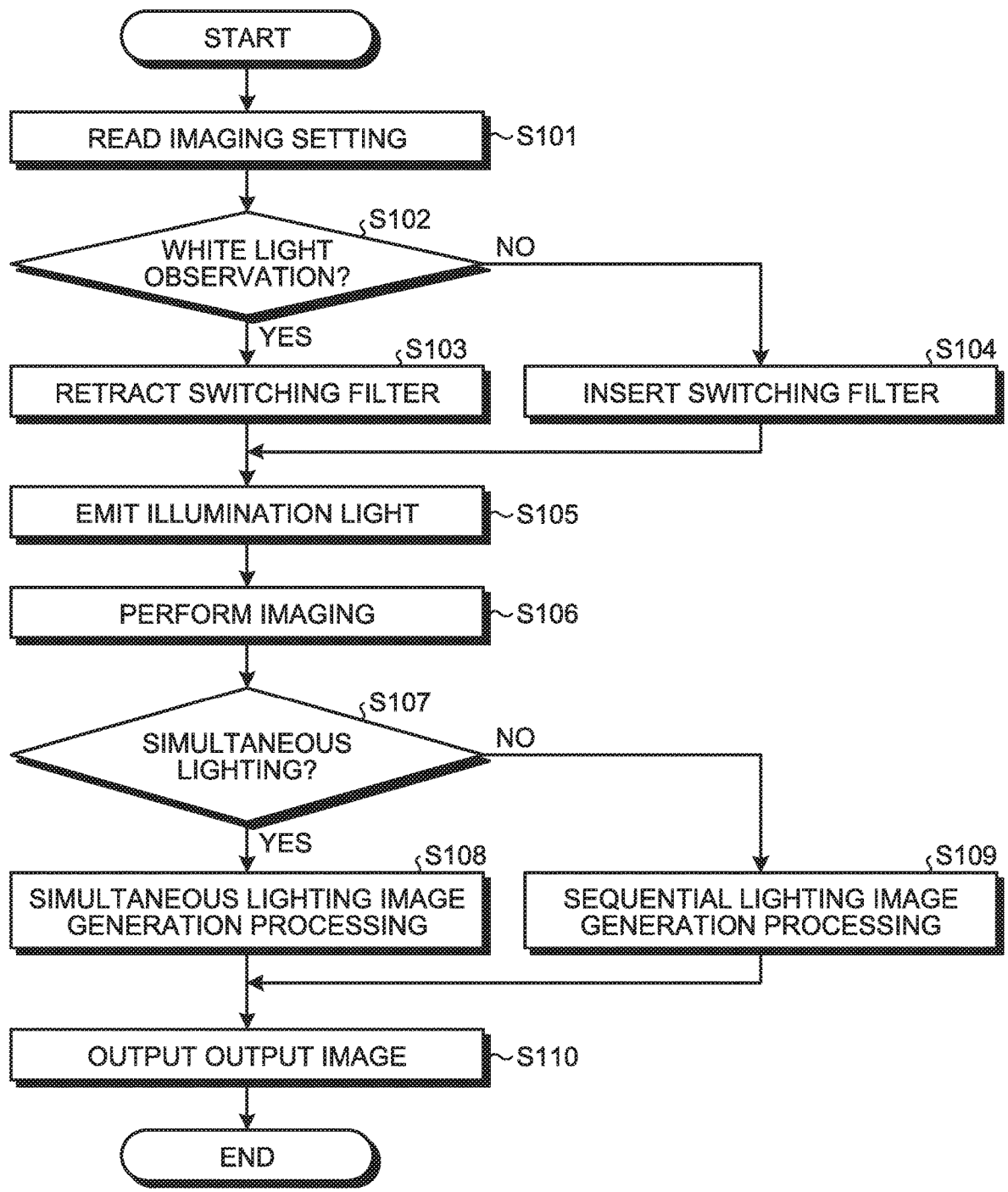
FIG. 13 is a flowchart illustrating an outline of processing that is executed by the endoscope device according to the second embodiment of the disclosure.

FIG. 13 is a flowchart illustrating the outline of the processing that is executed by the endoscope device 1A.

As illustrated in FIG. 13, first, in a case where the endoscope 2A, the light source unit 3A, and the processor unit 4 are connected to each other, and the imaging is ready to be started, the control unit 44 reads a drive mode or an observation mode of the light source unit 3A, and imaging setting relevant to the imaging of the image sensor 201 (Step S101).

Subsequently, the light source drive switching unit 441 determines whether or not the observation mode is the white light observation (Step S102), and in a case where the observation mode is the white light observation (Step S102: Yes), the light source drive switching unit 441 drives the drive unit 31d through the illumination controller 32, and thus, retracts the switching filter 31c from the light path of the illumination light that is emitted from the light source 31a (Step S103). In contrast, in a case where the observation mode is not the white light observation (Step S102: No), the light source drive switching unit 441 drives the drive unit 31d through the illumination controller 32, and thus, inserts the switching filter 31c onto the light path of the illumination light that is emitted from the light source 31a (Step S104).

After Step S103 or Step S104, the light source drive switching unit 441 allows the illumination light to exit from the light source unit 3A in a mode that is set in Step S101 described above (Step S105).

Subsequently, the endoscope 2A performs the imaging with respect to the subject that is irradiated with the illumination light by the light source unit 3A (Step S106).

After that, the image processing controller 442 determines whether or not the mode of the light source unit 3A is the simultaneous lighting (Step S107), and in a case where the mode of the light source unit 3A is the simultaneous lighting (Step S107: Yes), the image processing controller 442 executes simultaneous lighting image generation processing of allowing the simultaneous lighting image generating unit 411 to generate the output image by using the imaging signal that is generated by the endoscope 2A (Step S108). After Step S108, the endoscope device 1A proceeds to Step S110 described below. Note that, the details of the simultaneous lighting image generation processing will be described below.

In Step S107, in a case where the mode of the light source unit 3A is not the simultaneous lighting (Step S107: No), the image processing controller 442 executes sequential lighting image generation processing of allowing the sequential lighting image generating unit 412 to generate the output image by using the imaging signal that is generated by the endoscope 2A (Step S109). After Step S109, the endoscope device 1A proceeds to Step S110 described below. Note that, the details of the sequential lighting image generation processing will be described below.

Subsequently, the output image that is generated by the simultaneous lighting image generating unit 411 or the sequential lighting image generating unit 412 is output to the display unit 5 (Step S110). After Step S110, the endoscope device 1A ends the processing.

Details of Simultaneous Lighting Image Generation Processing

Next, the details of the simultaneous lighting image generation processing in Step S108 described above will be described.

Figure 14:
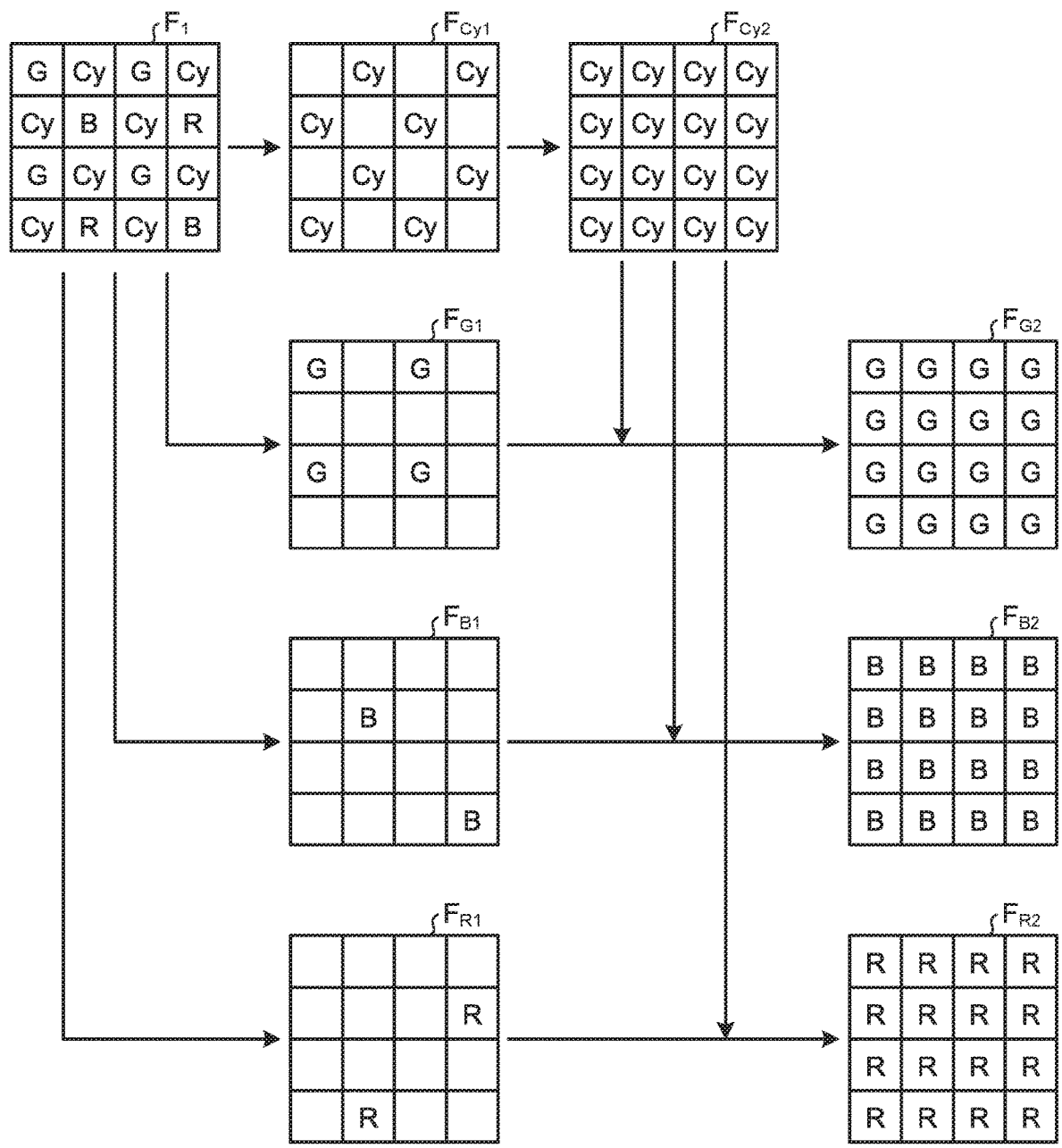
FIG. 14 is a schematic diagram illustrating an outline of simultaneous lighting image generation processing that is performed by a simultaneous lighting image generating unit, at the time of the white light observation of the endoscope device according to the second embodiment of the disclosure.

First, the simultaneous lighting image generation processing that is performed by the simultaneous lighting image generating unit 411 at the time of the white light observation of the endoscope device 1A will be described. FIG. 14 is a schematic diagram illustrating the outline of the simultaneous lighting image generation processing that is performed by the simultaneous lighting image generating unit 411, at the time of the white light observation of the endoscope device 1A.

As illustrated in FIG. 14, the simultaneous lighting image generating unit 411 performs the interpolation processing with respect to an image $F_1$ corresponding to the imaging signal generated by the endoscope 2A in which the primary pixel and the complementary pixel are mixed, by using an image $F_{Cy1}$ of a Cy pixel with the largest number of pixels, and thus, generates a Cy interpolation image $F_{Cy2}$ of the Cy pixel. Then, as illustrated in FIG. 14, the simultaneous lighting image generating unit 411 performs the interpolation processing with respect to each of an image $F_{G1}$, an image $F_{B1}$, and an image $F_{R1}$ by using the information of the Cy interpolation image $F_{Cy2}$ (a guide image) as a guide, and thus, generates each of a B interpolation image $F_{G2}$, a G interpolation image $F_{B2}$, and an R interpolation image $F_{R2}$. Here, known joint bilateral interpolation processing, guided filter interpolation processing, and the like are exemplified as the interpolation processing using the guide image.

Figure 15:
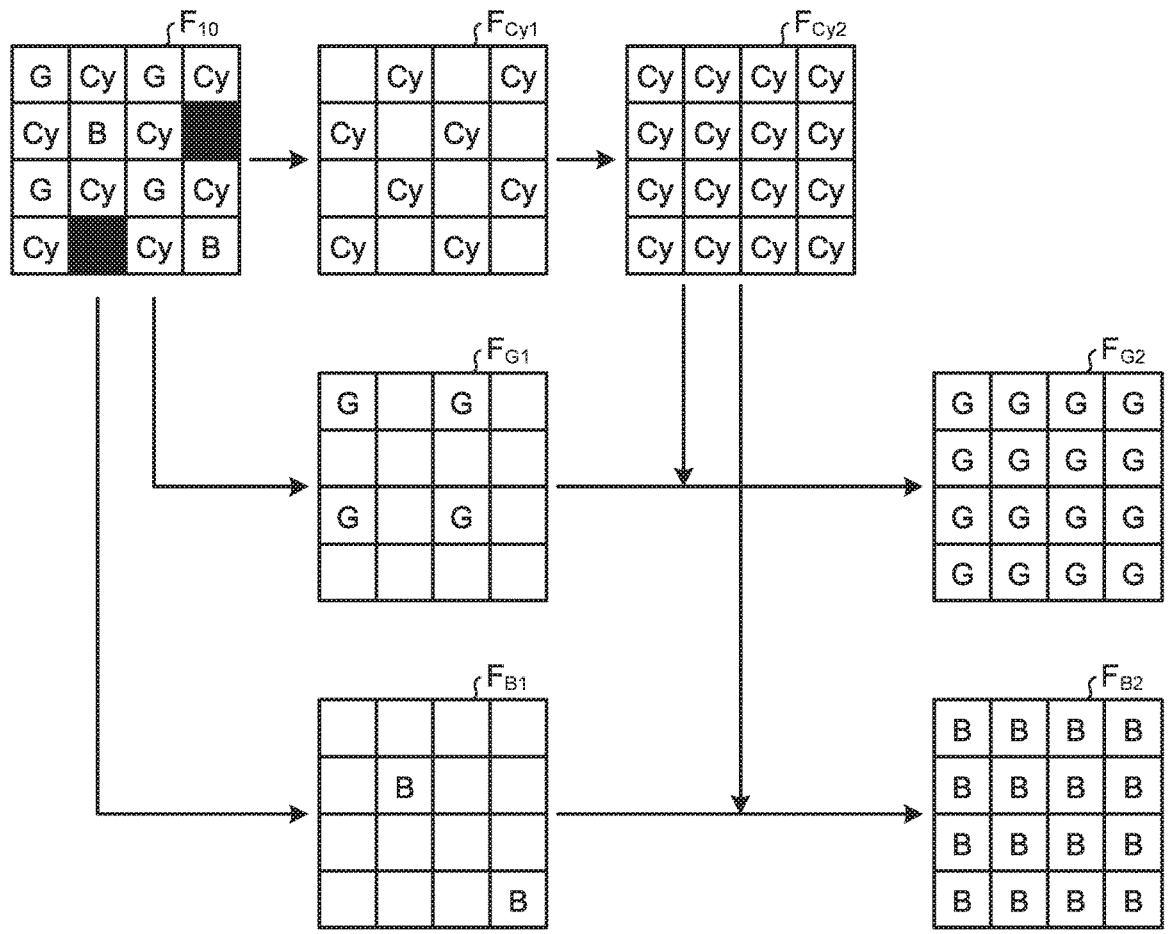
FIG. 15 is a schematic diagram illustrating the outline of the simultaneous lighting image generation processing that is performed by the simultaneous lighting image generating unit, at the time of the narrowband light observation of the endoscope device according to the second embodiment of the disclosure.

Next, the simultaneous lighting image generation processing that is performed by the simultaneous lighting image generating unit 411 at the time of the narrowband light observation of the endoscope device 1A will be described. FIG. 15 is a schematic diagram illustrating the outline of the simultaneous lighting image generation processing that is performed by the simultaneous lighting image generating unit 411, at the time of the narrowband light observation of the endoscope device 1A.

As illustrated in FIG. 15, the simultaneous lighting image generating unit 411 performs the interpolation processing with respect to an image $F_{10}$ corresponding to the imaging signal generated by the endoscope 2A in which the primary pixel and the complementary pixel are mixed, by using the image $F_{Cy1}$ of the Cy pixel with the largest number of pixels, and thus, generates the Cy interpolation image $F_{Cy2}$ of the Cy pixel. Then, as illustrated in FIG. 15, the simultaneous lighting image generating unit 411 performs the interpolation processing with respect to each of the image $F_{G1}$ and the image $F_{B1}$ by using the information of the Cy interpolation image $F_{Cy2}$ (the guide image) as a guide, and thus, generates each of the B interpolation image $F_{G2}$ and the G interpolation image $F_{B2}$. In the narrowband light observation, as illustrated in FIG. 15, there is no illumination light in the red wavelength band $H_R$, and thus, the R pixel is not capable of acquiring a signal value, and each of the B interpolation image $F_{G2}$ and the G interpolation image $F_{B2}$ is output as a pseudo color image. For this reason, the simultaneous lighting image generating unit 411 does not generate the R interpolation image $F_{R2}$.

As described above, the simultaneous lighting image generating unit 411 generates the G interpolation image and the B interpolation image from an imaging signal corresponding to one frame. As a result thereof, in principle, it is possible to prevent a color shift from occurring in the output image that is output from the simultaneous lighting image generating unit 411.

Details of Sequential Lighting Image Generation Processing

Next, the details of the sequential lighting image generation processing in Step S109 described above will be described. Note that, the sequential lighting image generation processing that is performed by the sequential lighting image generating unit 412 is different for each frame, and thus, the sequential lighting image processing for each frame will be described.

Figure 16:
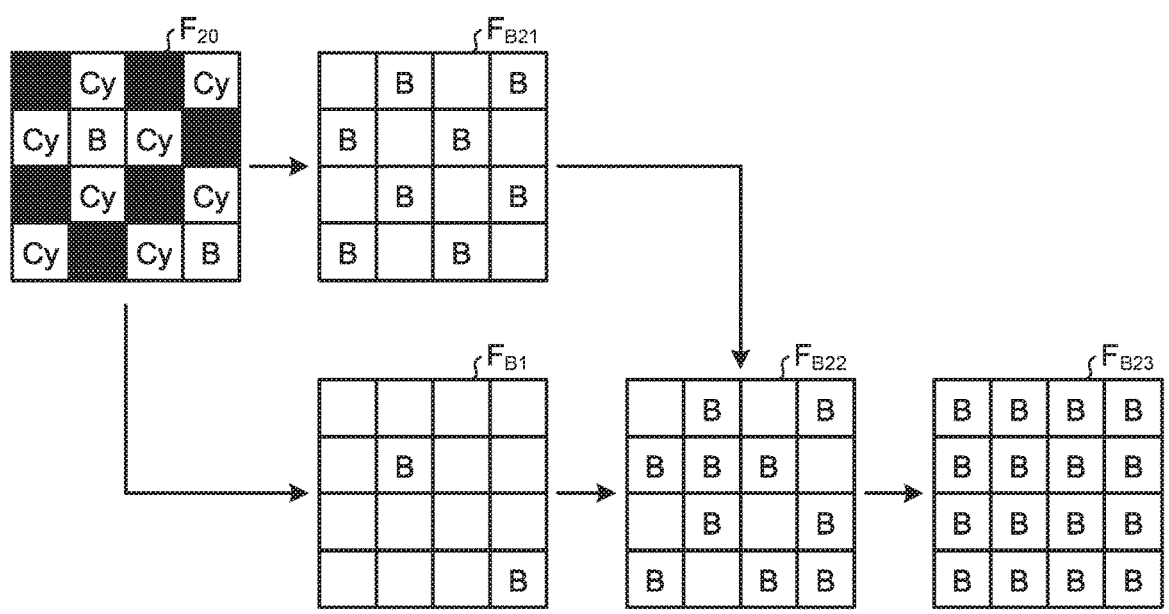
FIG. 16 is a schematic diagram illustrating an outline of sequential lighting image generation processing that is performed by a sequential lighting image generating unit when illumination light is emitted from an LED_B, at the time of the white light observation of the endoscope device according to the second embodiment of the disclosure.
Figure 17:
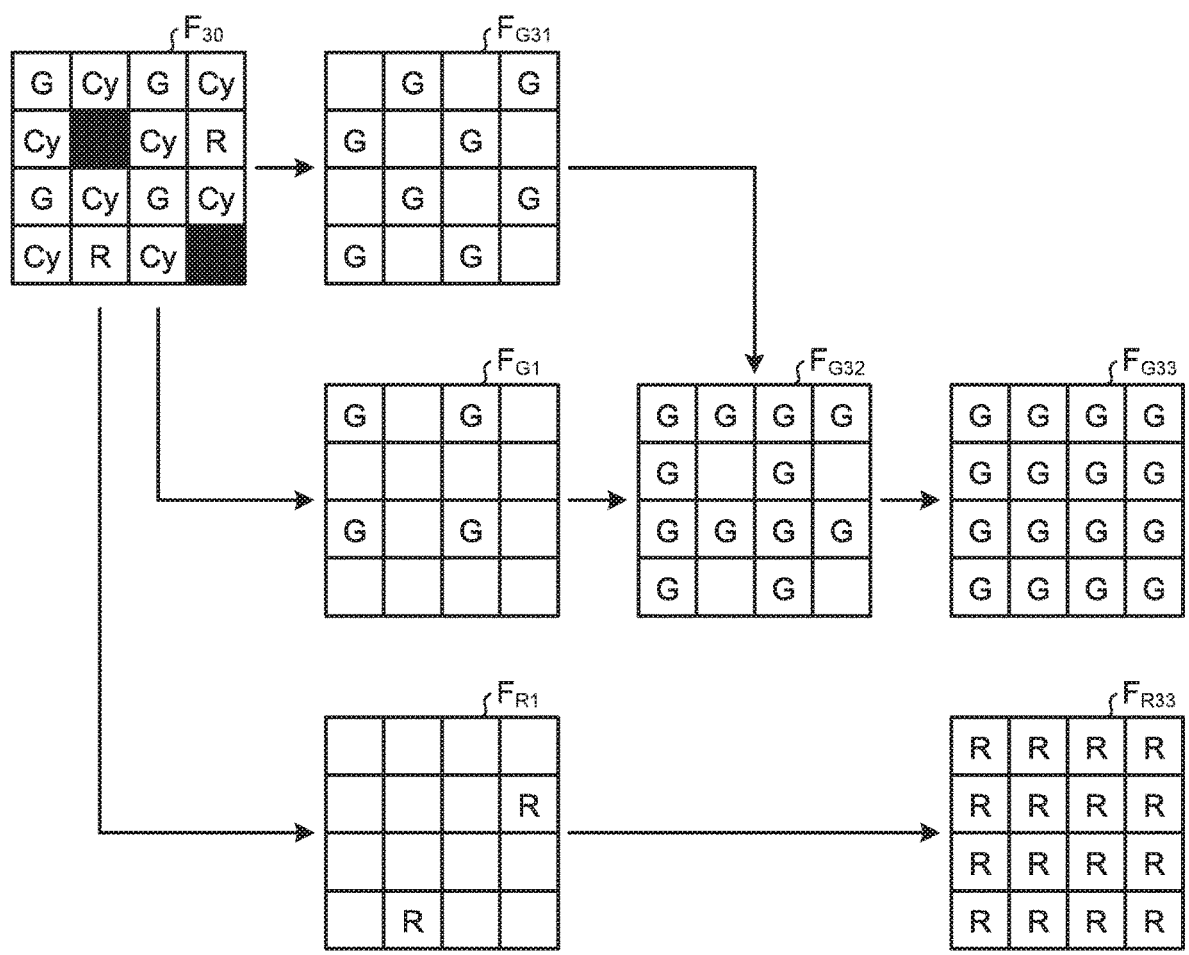
FIG. 17 is a schematic diagram illustrating the outline of the sequential lighting image generation processing that is performed by the sequential lighting image generating unit when the illumination light is emitted from an LED_G and an LED_R, at the time of the white light observation of the endoscope device according to the second embodiment of the disclosure.

First, the sequential lighting image generation processing that is performed by the sequential lighting image generating unit 412 at the time of the white light observation of the endoscope device 1A will be described. FIG. 16 is a schematic diagram illustrating the outline of the sequential lighting image generation processing that is performed by the sequential lighting image generating unit 412 when the illumination light is emitted from the LED 31a_B, at the time of the white light observation of the endoscope device 1A. FIG. 17 is a schematic diagram illustrating the outline of the sequential lighting image generation processing that is performed by the sequential lighting image generating unit 412 when the illumination light is emitted from the LED 31a_G and the LED 31a_R, at the time of the white light observation of the endoscope device 1A.

As illustrated in FIG. 16, in an image $F_{20}$ corresponding to an imaging signal of a frame in which only the LED 31a_B is irradiated with the light source unit 3A, a pixel that is capable of obtaining image information (the signal value) is only the Cy pixel and the B pixel. The Cy pixel has a sensitivity only in the blue wavelength band $H_B$, and thus, the Cy pixel can be regarded as the B pixel. The sequential lighting image generating unit 412 is not capable of acquiring the image information of each of the G pixel and the R pixel. For this reason, the sequential lighting image generating unit 412 performs interpolation processing such as known bilinear interpolation processing, cubic interpolation processing, and direction determination interpolation processing, by using an image $F_{B21}$ and an image $F_{B1}$, and thus, generates a B interpolation image $F_{B22}$ including image information of B information in the position of all of the pixels.

In addition, as illustrated in FIG. 17, in an image $F_{30}$ corresponding to an imaging signal of a frame in which only the LED 31a_G and the LED 31a_R are irradiated with the light source unit 3A, the pixel that is capable of obtaining the image information (the signal value) is only the Cy pixel, the G pixel, and the R pixel. The Cy pixel has a sensitivity in the green wavelength band $H_G$, and thus, the Cy pixel can be regarded as the G pixel. The sequential lighting image generating unit 412 performs the same interpolation processing as that of the frame in which only the LED 31a_B is irradiated with the light source unit 3A described above, by using an image $F_{G32}$, and thus, generates a G interpolation image $F_{G33}$ including image information of G information in the position of all of the pixels. Further, the sequential lighting image generating unit 412 performs the same interpolation processing as that of the frame in which only the LED 31a_B is irradiated with the light source unit 3A described above, by using the image $F_{R1}$, and thus, generates an R interpolation image $F_{R33}$ including image information of R information in the position of all of the pixels.

Then, the sequential lighting image generating unit 412 generates the output image by using the B interpolation image $F_{B22}$ of the frame in which only the LED 31a_B is irradiated with the light source unit 3A, and the G interpolation image $F_{G33}$ and the R interpolation image $F_{R33}$ of the frame in which only the LED 31a_G and the LED 31a_R are irradiated with the light source unit 3A, and outputs the image to the display unit 5.

Figure 18:
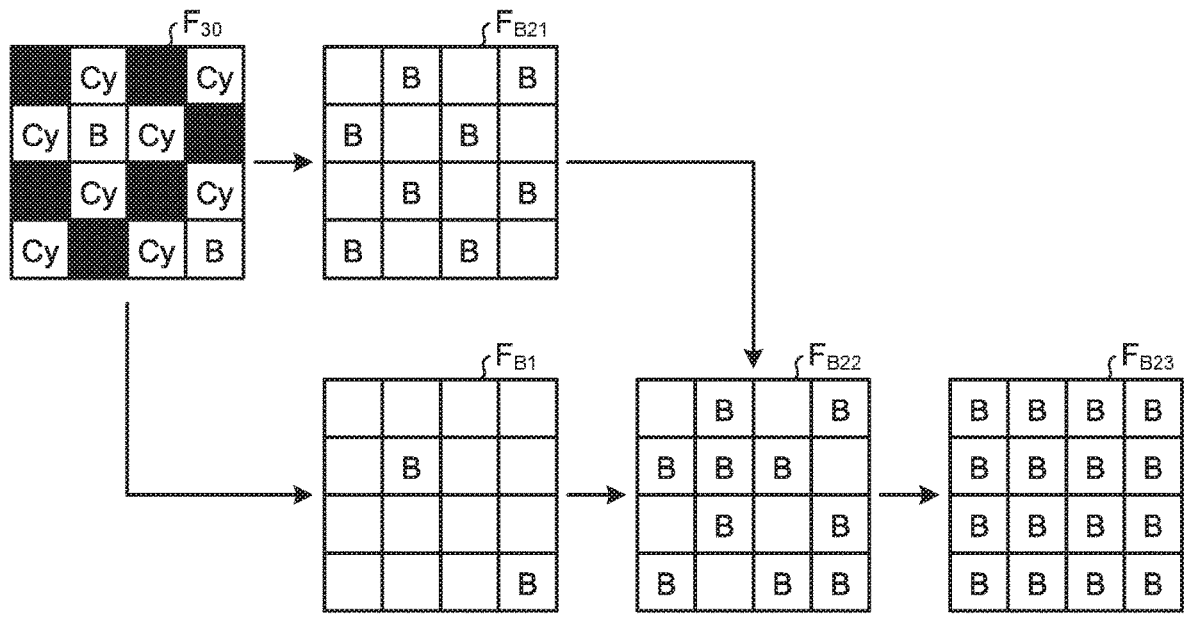
FIG. 18 is a schematic diagram illustrating the outline of the sequential lighting image generation processing that is performed by the sequential lighting image generating unit when the illumination light is emitted from the LED_B, at the time of the narrowband light observation of the endoscope device according to the second embodiment of the disclosure.
Figure 19:
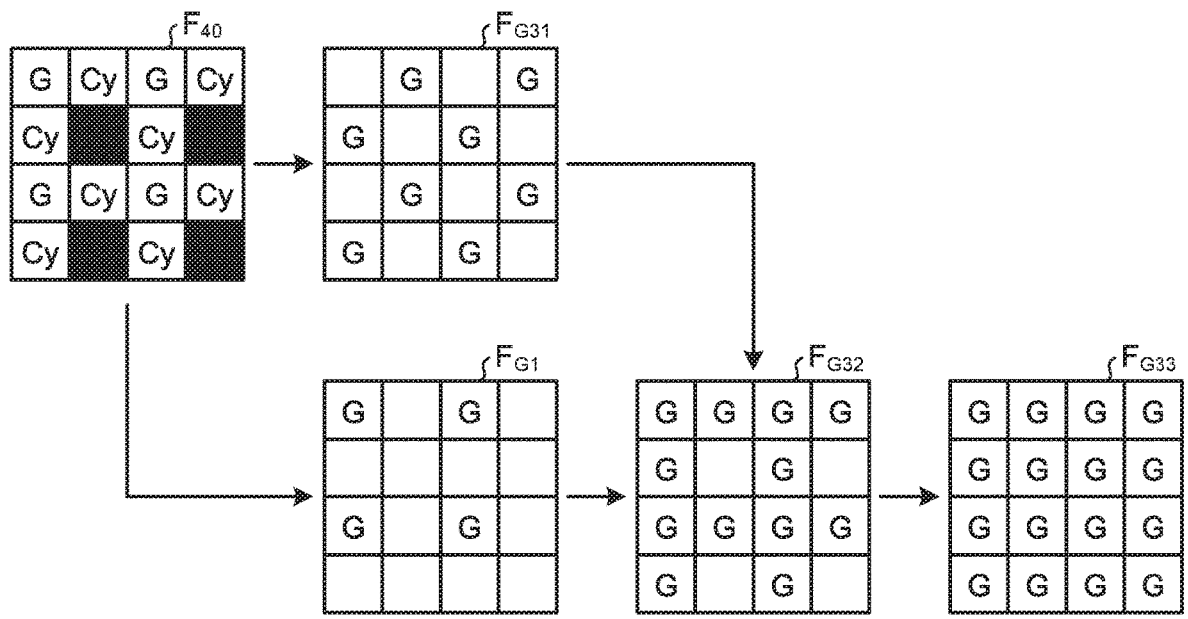
FIG. 19 is a schematic diagram illustrating the outline of the sequential lighting image generation processing that is performed by the sequential lighting image generating unit when the illumination light is emitted from the LED_G and the LED_R, at the time of the narrowband light observation of the endoscope device according to the second embodiment of the disclosure.

Next, the sequential lighting image generation processing that is performed by the sequential lighting image generating unit 412 at the time of the narrowband light observation of the endoscope device 1A will be described. FIG. 18 is a schematic diagram illustrating the outline of the sequential lighting image generation processing that is performed by the sequential lighting image generating unit 412 when the illumination light is emitted from the LED 31a_B, at the time of the narrowband light observation of the endoscope device 1A. FIG. 19 is a schematic diagram illustrating the outline of the sequential lighting image generation processing that is performed by the sequential lighting image generating unit 412 when the illumination light is emitted from the LED 31a_G and the LED 31a_R, at the time of the narrowband light observation of the endoscope device 1A.

As illustrated in FIG. 18, in the image $F_{30}$ corresponding to the imaging signal of the frame in which only the LED 31a_B is irradiated with the light source unit 3A, the pixel that is capable of obtaining the image information (the signal value) is only the Cy pixel and the B pixel. The Cy pixel has a sensitivity only in the blue wavelength band $H_B$, and thus, the Cy pixel can be regarded as the B pixel. The sequential lighting image generating unit 412 is not capable of acquiring the image information of each of the G pixel and the R pixel. For this reason, the sequential lighting image generating unit 412 performs interpolation processing such as known bilinear interpolation processing, cubic interpolation processing, and direction determination interpolation processing, by using an image $F_{B21}$ and an image $F_{B1}$, and thus, generates a B interpolation image $F_{B22}$ including image information of B information in the position of all of the pixels.

In addition, as illustrated in FIG. 19, in an image F40 corresponding to the imaging signal of the frame in which only the LED 31a_G and the LED 31a_R are irradiated with the light source unit 3A, the pixel that is capable of obtaining the image information (the signal value) is only the Cy pixel and the G pixel. The Cy pixel has a sensitivity in the green wavelength band $H_G$, and thus, the Cy pixel can be regarded as the G pixel. The sequential lighting image generating unit 412 performs the same interpolation processing as that of the frame in which only the LED 31a_B is irradiated with the light source unit 3A described above, by using an image $F_{G32}$, and thus, generates a G interpolation image $F_{G33}$ including image information of G information in the position of all of the pixels.

Then, the sequential lighting image generating unit 412 generates an output image of a pseudo color by using the B interpolation image $F_{B23}$ of the frame in which only the LED 31a_B is irradiated with the light source unit 3A, and the G interpolation image $F_{G33}$ of the frame in which only the LED 31a_G is irradiated with the light source unit 3A, and outputs the image to the display unit 5.

As described above, each of the LED 31a_B, the LED 31a_G, and the LED 31a_R is irradiated with the light source unit 3A in different frames, and thus, the sequential lighting image generating unit 412 is capable of generating the output image that is excellent in color separation performance, compared to the output image that is generated by the simultaneous lighting image generating unit 411.

Further, the sequential lighting image generating unit 412 performs the interpolation processing by regarding the Cy pixel as the B pixel or the G pixel, and thus, the number of pixels required to be calculated by correction processing is small, compared to the processing of the simultaneous lighting image generating unit 411, and therefore, it is also possible to perform the interpolation processing with a high accuracy. That is, the sequential lighting image generating unit 412 is capable of generating the output image having excellent resolution, compared to the output image that is generated by the simultaneous lighting image generating unit 411. The reason that the resolution of the output image that is generated by the sequential lighting image generating unit 412 is excellent is because many complementary filters are disposed on the image sensor 201. For this reason, in a general Bayer array, it is not possible to improve the resolution.

According to the second embodiment of the disclosure described above, in the case of performing the white light observation mode and the narrowband light observation mode, it is possible to generate the output image without a color shift that is captured in the simultaneous lighting and the output image excellent in the color separation and the resolution that is captured in the sequential lighting, even at the time of using the image sensor in which the primary pixel and the complementary pixel are mixed.

Third Embodiment

Next, a third embodiment of the disclosure will be described. The third embodiment is different from the second embodiment described above in the configuration of the endoscope device 1A. Specifically, in the third embodiment, the situation of the endoscope is detected on the basis of the imaging signal, and the sequential lighting and the simultaneous lighting are switched in accordance with a detection result. Hereinafter, the configuration of an endoscope device according to the third embodiment will be described, and then, processing that is executed by the endoscope device according to the third embodiment will be described. Note that, the same reference numerals will be applied to the same configurations as those of the second embodiment described above, and the detailed description thereof will be omitted.

Configuration of Endoscope Device

Figure 20:
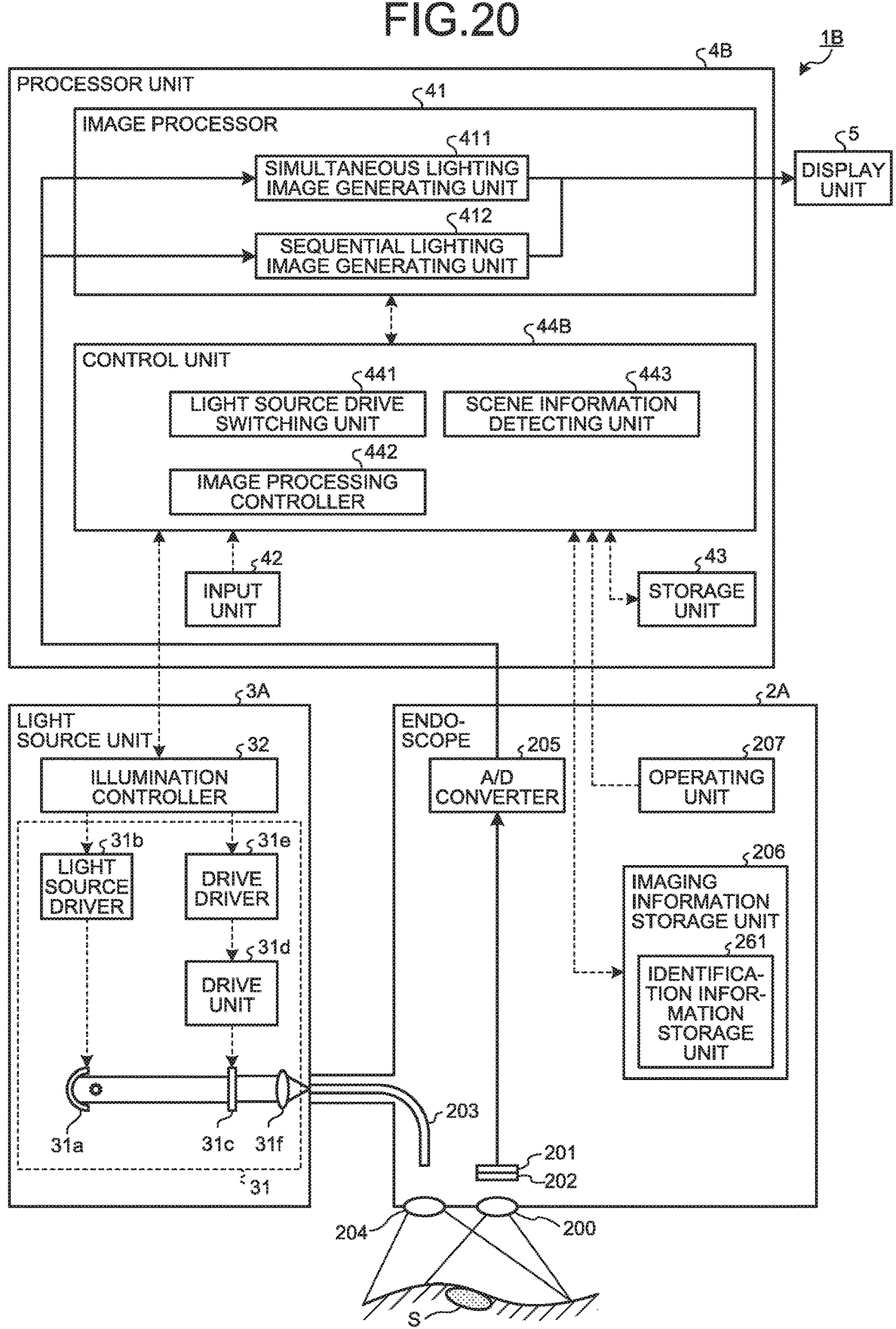
FIG. 20 is a schematic diagram illustrating a schematic configuration of an endoscope device according to a third embodiment of the disclosure.

FIG. 20 is a schematic diagram illustrating a schematic configuration of the endoscope device according to the third embodiment of the disclosure. An endoscope device 1B illustrated in FIG. 20 includes a processor unit 4B, instead of the processor unit 4 according to the second embodiment described above. The processor unit 4B includes a control unit 44B, instead of the control unit 44 according to the second embodiment described above.

The control unit 44B further includes a scene information detecting unit 443, in addition to the configuration of the control unit 44 according to the second embodiment described above.

The scene information detecting unit 443 detects a motion amount, on the basis of an imaging signal that is generated by the endoscope 2A. For example, the scene information detecting unit 443 detects a motion amount of a scene that is captured by the endoscope 2, on the basis of temporally successive imaging signals that are generated by the endoscope 2A.

Processing of Endoscope Device

Next, the processing that is executed by the endoscope device 1B will be described.

Figure 21:
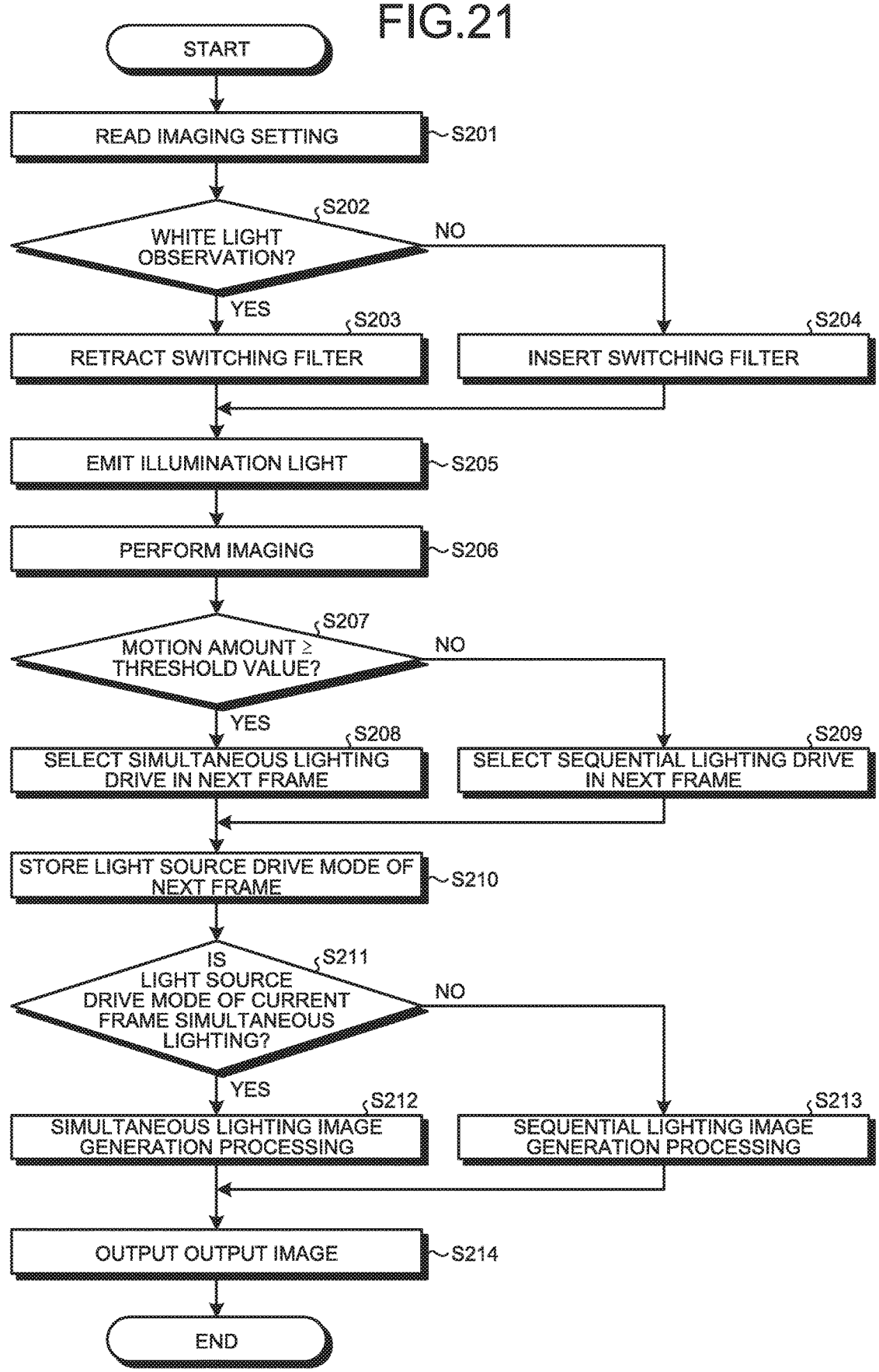
FIG. 21 is a flowchart illustrating an outline of processing that is executed by the endoscope device according to the third embodiment of the disclosure.

FIG. 21 is a flowchart illustrating the outline of the processing that is executed by the endoscope device 1B. In FIG. 21, Step S201 to Step S206 respectively correspond to Step S101 to Step S106 of FIG. 13 described above.

In Step S207, the scene information detecting unit 443 calculates a difference between imaging information of the previous frame and imaging information of the current frame, and compares the calculated motion amount with a predetermined threshold value (Step S207), and in a case where the scene information detecting unit 443 determines that the motion amount is greater than or equal to a predetermined threshold value (Step S207: Yes), the light source drive switching unit 441 selects the simultaneous lighting as a light source drive mode of the next frame (Step S208). After Step S208, the endoscope device 1B proceeds to Step S210 described below. In contrast, in a case where the scene information detecting unit 443 determines that the motion amount is not greater than or equal to the predetermined threshold value (Step S207: No), the light source drive switching unit 441 selects the sequential lighting as the light source drive mode of the next frame (Step S209). After Step S209, the endoscope device 1B proceeds to Step S210 described below.

In Step S210, the light source drive switching unit 441 stores the light source drive mode of the next frame in the storage unit 43. After Step S210, the endoscope device 1B proceeds to Step S211.

In Step S211, in a case where the light source drive mode of the current frame is the simultaneous lighting (Step S211: Yes), the endoscope device 1B proceeds to Step S212, and in a case where the light source drive mode of the current frame is not the simultaneous lighting (Step S211: No), the endoscope device 1B proceeds to Step S213.

Step S212 to Step S214 respectively correspond to Step S108 to Step S110 of FIG. 13 described above. After Step S214, the endoscope device 1B ends the processing.

According to the third embodiment of the disclosure described above, in the case of performing the white light observation mode and the narrowband light observation mode, it is possible to generate an image having excellent image quality in both of the simultaneous lighting and the sequential lighting, even at the time of using the image sensor in which the primary pixel and the complementary pixel are mixed.

In addition, according to the third embodiment of the disclosure, the light source drive switching unit 441 switches the mode of the light source unit 3A, in accordance with the motion amount that is detected by the scene information detecting unit 443, and thus, it is possible to omit a switching operation of the user.

Note that, in the third embodiment of the disclosure, the scene information detecting unit 443 detects the motion amount, but the disclosure is not limited thereto. For example, the scene information detecting unit 443 may detect an edge amount by performing edge extraction processing with respect to the imaging signal that is generated by the endoscope 2A. In this case, in a case where the edge amount that is detected by the scene information detecting unit 443 is greater than or equal to a predetermined threshold value, that is, an abnormal spot with less motion in the scene captured by the endoscope 2A, for example, a lesion is highly likely to be observed, and thus, the light source drive switching unit 441 allows the light source unit 3A to execute the sequential lighting, and in a case where the edge amount that is detected by the scene information detecting unit 443 is not greater than or equal to the predetermined threshold value, the light source drive switching unit 441 allows the light source unit 3A to execute the simultaneous lighting.

In addition, in the third embodiment of the disclosure, the scene information detecting unit 443 may automatically detect an abnormal region included in the image corresponding to the imaging signal that is generated by the endoscope 2A. For example, the scene information detecting unit 443 may detect whether or not there is the abnormal region, with respect to the image corresponding to the imaging signal that is generated by the endoscope 2A, and the image corresponding to the imaging signal that is continuously generated by the endoscope 2A, by using the model of the abnormal region or pattern matching that is learned in advance. Here, the abnormal region is a lesion region, a bleeding region, and a region having a luminance or a chromaticness of greater than or equal to a predetermined threshold value. In a case where the scene information detecting unit 443 detects the abnormal region, that is, the abnormal spot with less motion in the scene captured by the endoscope 2A, for example, a lesion is highly likely to be observed, and thus, the light source drive switching unit 441 allows the light source unit 3A to execute the sequential lighting, and in a case where the scene information detecting unit 443 does not detect the abnormal region, the light source drive switching unit 441 allows the light source unit 3A to execute the simultaneous lighting.

In addition, in the third embodiment of the disclosure, the scene of the endoscope device 1A is detected on the basis of the imaging signal that is generated by the endoscope 2A, but the disclosure is not limited thereto, and a detection sensor (not illustrated) such as an acceleration sensor or a gyro sensor may be provided on a distal end portion of the endoscope 2A (not illustrated), and the scene information detecting unit 443 may detect the motion amount of the endoscope 2A, on the basis of a detection result of the detection sensor. In this case, in a case where the motion amount that is detected by the scene information detecting unit 443 is greater than or equal to a predetermined threshold value, the light source drive switching unit 441 allows the light source unit 3A to execute the simultaneous lighting, and in a case where the motion amount that is detected by the scene information detecting unit 443 is not greater than or equal to the predetermined threshold value, the light source drive switching unit 441 allows the light source unit 3A to execute the sequential lighting.

In addition, in the third embodiment of the disclosure, the scene information detecting unit 443 may detect a focal distance of the imaging optical system 200. In a case where the imaging optical system 200 is capable of performing twofold magnification observation, the light source drive switching unit 441 allows the light source unit 3A to execute the simultaneous lighting when the focal distance that is detected by the scene information detecting unit 443 is greater than or equal to a predetermined threshold value (for example, when the focal distance of the imaging optical system 200 is twofold, and the endoscope 2A performs magnification observation), and the light source drive switching unit 441 allows the light source unit 3A to execute the sequential lighting when the focal distance that is detected by the scene information detecting unit 443 is not greater than or equal to the predetermined threshold value ((for example, when the focal distance of the imaging optical system 200 is onefold, and the endoscope 2 performs normal observation), the imaging optical system 200 performs twofold magnification observation of normal magnification observation).

In addition, in the third embodiment of the disclosure, the scene information detecting unit 443 may detect a usage condition of a treatment tool. In such a case, when the scene information detecting unit 443 detects the use of the treatment tool, the light source drive switching unit 441 allows the light source unit 3A to execute the simultaneous lighting, and when the scene information detecting unit 443 does not detect the use of the treatment tool (the imaging optical system 200 performs twofold magnification observation of the normal magnification observation), the light source drive switching unit 441 allows the light source unit 3A to execute the sequential lighting.

Other Embodiments

Figures 22, 23:
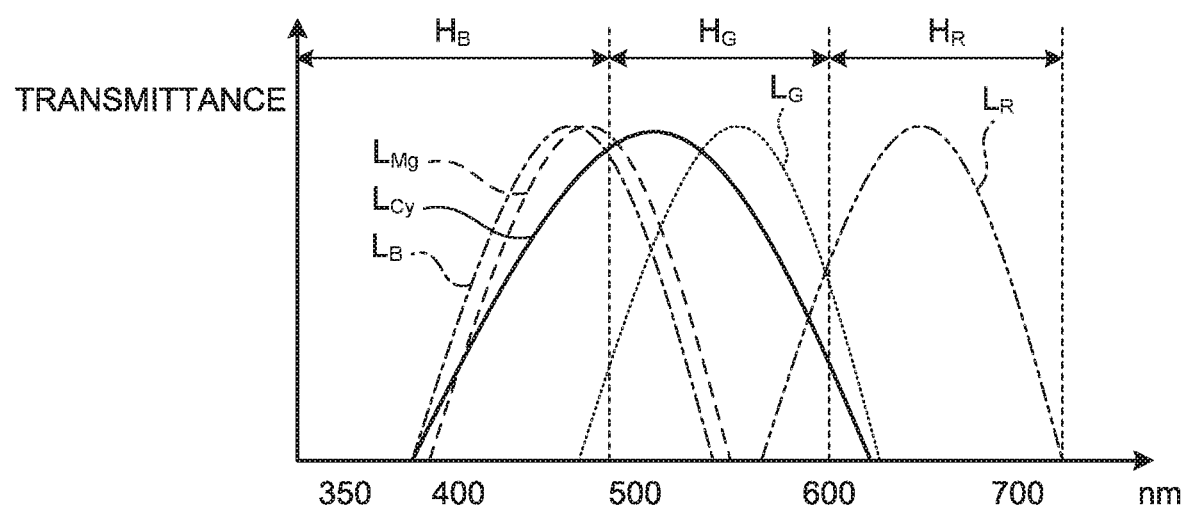
FIG. 22 is a schematic diagram illustrating an example of a configuration of a color filter according to a modification example of the first embodiment to the third embodiment.
FIG. 23 is a diagram illustrating an example of transmission properties of each filter configuring the color filter according to the modification example of the first embodiment to the third embodiment.

In the first embodiment to the third embodiment described above, it is possible to suitably change the configuration of the color filter. FIG. 22 is a schematic diagram illustrating an example of the configuration of a color filter according to a modification example of the first embodiment to the third embodiment. As illustrated in FIG. 22, in a color filter 202C, a filter unit U2 including 16 filters arranged into the shape of a two-dimensional lattice of 4×4 is disposed in accordance with the disposition of the pixel $P_{ij}$. Specifically, an Mg filter is disposed, instead of the R filter of the color filter 202 described above. As illustrated in a curve $L_{Mg}$ of FIG. 23, an Mg pixel receives the light in the blue wavelength band $H_B$ and the light in the green wavelength band $H_G$.

Figure 24:
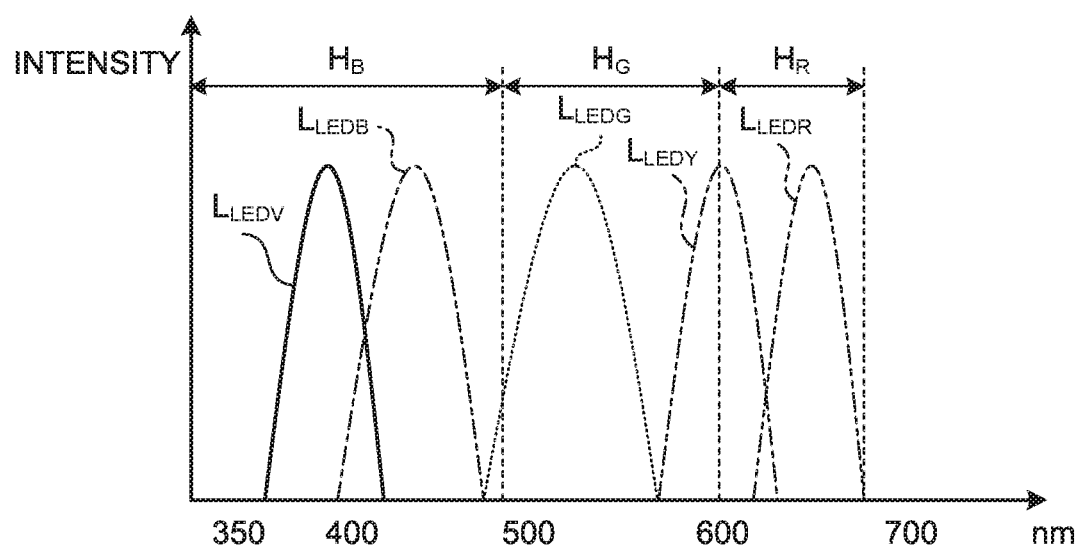
FIG. 24 is a diagram illustrating an example of spectroscopic properties of each light source of a light source unit according to the modification example of the first embodiment to the third embodiment.

In addition, in the first embodiment to the third embodiment described above, there may be four types of illumination light rays that are emitted from the light source unit. For example, as illustrated in a curve $L_{LEDV}$ and a curve $L_{LEDY}$ of FIG. 24, the light source unit may further include five or more LEDs, for example, a light source that is capable of emitting light in a violet wavelength band and a light source that is capable of emitting light in a yellow wavelength band.

As described above, some embodiments of the disclosure have been described in detail, on the basis of the drawings, but the embodiments are an example, and the disclosure can be implemented in other forms in which various modifications and improvements are made on the basis of the knowledge of a person skilled in the art, including the aspects described in the disclosure of the disclosure.

In addition, in the embodiments of the disclosure, a flexible endoscope device has been described as an example, but the disclosure is not limited thereto, and a rigid endoscope device can also be applied. It is obvious that a capsule endoscope device or a microscope device can also be applied.

In addition, the "unit (a section, a module, and a unit)" described above can be replaced with "means", a "circuit", or the like. For example, the control unit can be replaced with control means or a control circuit.

According to the disclosure, an effect is obtained in which it is possible to generate an image having excellent image quality in both of simultaneous lighting and sequential lighting, even at the time of using an image sensor in which a primary pixel and a complementary pixel are mixed.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope device, comprising:
a light source configured to perform any one of simultaneous lighting and sequential lighting, the simultaneous lighting being simultaneously emitting a plurality of light rays of which at least wavelength bands are different from each other, the sequential lighting being individually emitting a plurality of light rays of which at least wavelength bands are different from each other;
an image sensor including a plurality of pixels disposed into a shape of a two-dimensional lattice, each pixel being configured to generate an imaging signal by receiving light and by performing photoelectric conversion;
a plurality of filters including at least one type of primary filter and a complementary filter, the at least one type of primary filter being configured to transmit light in any one wavelength band of a red wavelength band, a green wavelength band, and a blue wavelength band, the complementary filter being configured to transmit light in the green wavelength band and transmits light in one wavelength band of the red wavelength band and the blue wavelength band, each of the plurality of filters being disposed to correspond to each of the plurality of pixels; and
a processor comprising hardware, the processor being configured to
cause the light source to switch between the simultaneous lighting and the sequential lighting,
when the simultaneous lighting is performed, perform interpolation processing to generate an output image by using an imaging signal generated from a pixel corresponding to the complementary filter, and
when the sequential lighting is performed, perform interpolation processing to generate an output image by using an imaging signal generated from a pixel corresponding to the complementary filter as an imaging signal generated from a pixel corresponding to the at least one type of primary filter.

2. The endoscope device according to claim 1,
wherein the light source is configured to emit each of blue light having a peak intensity in the blue wavelength band and green light having a peak intensity in the green wavelength band, and
the processor is configured to cause the light source to alternately emit the blue light and the green light when the light source executes the sequential lighting.

3. The endoscope device according to claim 1,
wherein the processor is configured to cause the light source to switch a mode of the light source in accordance with input of an instruction signal for giving an instruction on any one of the simultaneous lighting and the sequential lighting.

4. The endoscope device according to claim 1,
wherein the processor is further configured to detect a scene of the endoscope device, and cause the light source to switch a mode of the light source, based on a detection result.

5. The endoscope device according to claim 4,
wherein the processor is configured to
detect a motion amount, based on the imaging signal,
when the motion amount is greater than or equal to a predetermined threshold value, cause the light source to execute the simultaneous lighting, and
when the motion amount is not greater than or equal to the predetermined threshold value, cause the light source to execute the sequential lighting.

6. The endoscope device according to claim 4,
wherein the processor is configured to
detect an edge amount, based on of the imaging signal,
when the edge amount is greater than or equal to a predetermined threshold value, cause the light source to execute the sequential lighting, and
when the edge amount is not greater than or equal to the predetermined threshold value, cause the light source to execute the simultaneous lighting.

7. The endoscope device according to claim 4,
wherein the processor is configured to detect an abnormal region included in an image corresponding to the imaging signal,
when the abnormal region is detected, cause the light source to execute the sequential lighting, and
when the abnormal region is not detected, cause the light source to execute the simultaneous lighting.

8. The endoscope device according to claim 4, further comprising:
an endoscope that includes the image sensor in a distal end portion; and
a detector that is provided in the distal end portion, the detector being configured to detect a motion of the distal end portion,
wherein the processor is configured to
detect a motion amount of the endoscope, based on a detection result of the detector,
when the motion amount is greater than or equal to a predetermined threshold value, cause the light source to execute the simultaneous lighting, and
when the motion amount is not greater than or equal to the predetermined threshold value, cause the light source to execute the sequential lighting.

9. The endoscope device according to claim 4, further comprising:
an imaging optical system configured to change a focal distance, and form a subject image on a light receiving surface of the image sensor,
wherein the processor is configured to detect the focal distance of the imaging optical system,
when the focal distance is greater than or equal to a predetermined threshold value, cause the light source to execute the simultaneous lighting, and
when the focal distance is not greater than or equal to the predetermined threshold value, cause the light source to execute the sequential lighting.

10. An image processing method executed by an endoscope device including: a light source configured to perform any one of simultaneous lighting and sequential lighting, the simultaneous lighting being simultaneously emitting a plurality of light rays of which at least wavelength bands are different from each other, the sequential lighting being individually emitting a plurality of light rays of which at least wavelength bands are different from each other; an image sensor including a plurality of pixels disposed into a shape of a two-dimensional lattice, each pixel being configured to generate an imaging signal by receiving light and by performing photoelectric conversion; and a plurality of filters including at least one type of primary filter and a complementary filter, the at least one type of primary filter being configured to transmit light in any one wavelength band of a red wavelength band, a green wavelength band, and a blue wavelength band, the complementary filter being configured to transmit light in the green wavelength band and transmits light in one wavelength band of the red wavelength band and the blue wavelength band, each of the plurality of filters being disposed to correspond to each of the plurality of pixels, the method comprising:

switching between the simultaneous lighting and the sequential lighting, with respect to the light source;

when the simultaneous lighting is performed, performing interpolation processing to generate an output image by using an imaging signal generated from a pixel corresponding to the complementary filter; and when the sequential lighting is performed, performing interpolation processing to generate an output image by using an imaging signal generated from a pixel corresponding to the complementary filter as an imaging signal generated from a pixel corresponding to the at least one type of primary filter.

11. A non-transitory computer-readable recording medium in which an executable program is recorded, the program causing an endoscope device including: a light source configured to perform any one of simultaneous lighting and sequential lighting, the simultaneous lighting being simultaneously emitting a plurality of light rays of which at least wavelength bands are different from each other, the sequential lighting being individually emitting a plurality of light rays of which at least wavelength bands are different from each other; an image sensor including a plurality of pixels disposed into a shape of a two-dimensional lattice, each pixel being configured to generate an imaging signal by receiving light and by performing photoelectric conversion; and a plurality of filters including at least one type of primary filter and a complementary filter, the at least one type of primary filter being configured to transmit light in any one wavelength band of a red wavelength band, a green wavelength band, and a blue wavelength band, the complementary filter being configured to transmit light in the green wavelength band and transmits light in one wavelength band of the red wavelength band and the blue wavelength band, each of the plurality of filters being disposed to correspond to each of the plurality of pixels, to execute:

switching between the simultaneous lighting and the sequential lighting, with respect to the light source;

when the simultaneous lighting is performed, performing interpolation processing to generate an output image by using an imaging signal generated from a pixel corresponding to the complementary filter; and when the sequential lighting is performed, performing interpolation processing to generate an output image by using an imaging signal generated from a pixel corresponding to the complementary filter as an imaging signal generated from a pixel corresponding to the at least one type of primary filter.

\* \* \* \* \*